US012624075B2

(12) United States Patent (10) Patent No.: US 12,624,075 B2
Kurihara et al. (45) Date of Patent: May 12, 2026

(54) IMMUNE INDUCER

(71) Applicant: TORAY INDUSTRIES, INC., Tokyo (JP)

(72) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 642 days.

(21) Appl. No.: 17/972,055

(22) Filed: Oct. 24, 2022

(65) Prior Publication Data

US 2023/0190899 A1 Jun. 22, 2023

Related U.S. Application Data

(62) Division of application No. 15/743,869, filed as application No. PCT/JP2016/073077 on Aug. 5, 2016, now Pat. No. 11,510,971.

(30) Foreign Application Priority Data

Aug. 10, 2015 (JP) ................................ 2015-158539

(51) Int. Cl.
| | |
|---|---|
| A61K 39/00 | (2006.01) |
| A61K 35/15 | (2015.01) |
| A61K 35/17 | (2025.01) |
| A61K 35/76 | (2015.01) |
| A61K 39/39 | (2006.01) |
| A61K 45/00 | (2006.01) |
| A61K 48/00 | (2006.01) |
| A61P 35/00 | (2006.01) |
| C07K 14/47 | (2006.01) |
| C12N 5/10 | (2006.01) |
| C12N 15/09 | (2006.01) |

(52) U.S. Cl.
CPC .......... *C07K 14/4702* (2013.01); *A61K 35/15* (2013.01); *A61K 35/17* (2013.01); *A61K 35/76* (2013.01); *A61K 39/00* (2013.01); *A61K 39/0011* (2013.01); *A61K 39/39* (2013.01); *A61K 45/00* (2013.01); *A61K 48/00* (2013.01); *A61P 35/00* (2018.01); *C07K 14/47* (2013.01); *C12N 5/10* (2013.01); *C12N 15/09* (2013.01); *A61K 2039/5154* (2013.01); *A61K 2039/5158* (2013.01); *A61K 2039/53* (2013.01); *A61K 2039/572* (2013.01)

(58) Field of Classification Search
None
See application file for complete search history.

(56) References Cited

U.S. PATENT DOCUMENTS

| | | | | |
|---|---|---|---|---|
| 7,842,467 | B1 | 11/2010 | Heidbrink | |
| 10,251,942 | B2 * | 4/2019 | Kurihara | C12N 5/0639 |
| 11,510,971 | B2 * | 11/2022 | Kurihara | A61K 35/76 |
| 2004/0248218 | A1 | 12/2004 | Kasid et al. | |
| 2012/0177673 | A1 | 7/2012 | Kurihara et al. | |

FOREIGN PATENT DOCUMENTS

| | | |
|---|---|---|
| CN | 102481333 A | 5/2012 |
| EP | 2 213 301 A1 | 8/2010 |
| EP | 2 474 315 A1 | 7/2012 |
| RU | 2 529 373 C2 | 9/2012 |
| WO | WO 02/081641 A2 | 10/2002 |
| WO | WO 2009/054471 A1 | 4/2009 |
| WO | WO 2010/021112 A1 | 2/2010 |
| WO | WO 2011/027807 A1 | 3/2011 |
| WO | WO 2017/184590 A8 | 10/2017 |
| WO | WO 2017184590 A1 * | 10/2017 |

OTHER PUBLICATIONS

HLA Nomenclature (2023, 2 pages) (Year: 2023).*
Wieczorek et al ( (Front. Immunol., 2017, article 292: 1-16) (Year: 2017).*
Ochoa-Garay et al (Mal. Immunol. 1997, 34(3): 273-281) (Year: 1997).*
Celis et al (Mol. Immunol., 1994, 31(18): 1423-1430) (Year: 1994).*
Hassan et al (Mol. & cell. Proteomics, 2013, 10.74/mcp.M112. 024810: 1829-1843 and pp. 1, 18, 69, 93 and 234 of Supplementary Table S1) (Year: 2013).*
Caron et al (eLife, Jul. 2015, 4:e07661, pp. 1-17 plus pp. 1, 197, 236 and 249 of Figure 2/Table 3). (Year: 2015).*
Beatty and Gladney, Clin. Canc. Res. (2014), vol. 21, No. 4, pp. 687-692.
Berger et al., Int. J. Cancer (2004), vol. 111, pp. 229-237.
Bergman et al., J. Immunol. (1996), vol. 157, pp. 3242-3249.
Bourdetsky et al., PNAS, Plubl online Apr. 8, 2014, E1591-E1599, 2014.
Caron et al., eLife, Jul. 2015, 4:307661, pp. 1-17 (2015), + suppl pp. 18-611.
Celis et al., Mol. Immunol. (1994), vol. 31, No. 18, pp. 1423-1430.
Communication Pursuant to Article 94(3) EPC issued Sep. 2, 2020, in EP 16 835 086.6, 8 pages.
Dibrino et al., J. Immunology (1993), vol. 151, No. 11, pp. 5930-5935.
Eisenlohr et al., J. Exp. Med. (1992), vol. 175, pp. 481-487.

(Continued)

*Primary Examiner* — Michael Szperka
*Assistant Examiner* — Marianne Dibrino
(74) *Attorney, Agent, or Firm* — Birch, Stewart, Kolasch & Birch, LLP

(57) ABSTRACT

Provided is a novel peptide useful as an active ingredient in an agent for treating or preventing cancer, and to provide the use of the polypeptide as an immune inducer. The polypeptide binds to a MHC class I or class II molecule. The immune inducer contains as an active ingredient at least one polypeptide consisting of the amino acid sequence represented by one of SEQ ID NOs: 5-7, 9, 10, 12-15 and 17-34 or at least one polypeptide consisting of the amino acid sequence represented by one of SEQ ID NOs: 35-67. The immune inducer further comprises an effective amount of an adjuvant.

5 Claims, 8 Drawing Sheets

Specification includes a Sequence Listing.

(56)                    References Cited

OTHER PUBLICATIONS

Engelhard, V. H., Curr. Opin, Immunol. (1994), vol. 6, pp. 13-23.
English translation of Office Action issued Sep. 2, 2020, in Chinese Patent Application No. 201680043484.5, 8 pages.
English translation of Written Opinion of the International Searching Authority mailed Sep. 20, 2016, in PCT/JP2016/073077.
Extended European Search Report issued Feb. 22, 2019, in European Patent Application No. 16835086.6.
FasSEQ (Year: 2021), 1 page.
Gileadi et al., Eur. J. Immunol. (1999), vol. 29, pp. 2213-2222.
Guo et al., Nature (1992), vol. 360, pp. 364-366.
Hassan et al., Molecular & Cellular Proteomics (2013), 10.74/mcp. M112.024810: 1829-1843.
HLA Nomenclature (2015), 2 pages.
International Search Report, issued in PCT/JP2016/073077, PCT/ISA/210, dated Sep. 20, 2016.
Kalos and June, Immunity (2013), vol. 39. pp. 49-60.
Kerkar and Restifo, Cancer Res. (2012), vol. 72, No. 13, pp. 3125-3130.
Kumar et al. "SCC-112, a novel cell cycle-regulated molecule, exhibits reduced expression in human renal carcinomas", Gene, 2004, vol. 328, pp. 187-196.

Office Action issued Jan. 31, 2020, in Russian Patent Application No. 2018107330/10(011202), 15 pages.
Office Action issued Nov. 19, 2020, in Russian Patent Application No. 2018107330/10(011202), 9 pages.
Put et al., "PDS5A, a novel translocation partner of MLL in acute myeloid leukemia," Leukemia Research (2012), vol. 36, pp. e87-e89.
Reche and Reinherz, G. Nicosia et al., Eds, ICARIS 2004, LNCS 3239: 189-196, 2004.
Roit, I. et al. (2003) Immunology 5th Edition, St. Louis, Missouri: J.P. Lippincott, pp. 114-117.
Shastri et al., J. Immunol. (1995), vol. 155, pp. 4339-4346.
Speiser et al., Eur. J. Immunol. (2002), vol. 32, pp. 731-741.
Spranger, S., Int. Immunol. (2015), vol. 28, No. 8, pp. 383-391.
Theoboald et al., J. Exp. Med. (1998), vol. 188, No. 6, pp. 1017-1028.
Vitale et al., Eur. J. Immunol. (2014), vol. 44, pp. 1582-1592.
Wang et al., Cell Immunol. (1992), vol. 143, pp. 284-297.
Wieczorek et al., Front. Immunol. (2017), vol. 8, Article 292, pp. 1-16.
Office Action issued Sep. 2, 2020, in Chinese Patent Application No. 201680043484.5.
Roit, I. et al. (2003) Immunology 5th Edition, St. Louis, Missouri: J.P. Lippincott, pp. 159, 161-163.

* cited by examiner

IMMUNE INDUCER

CROSS-REFERENCE TO RELATED APPLICATIONS

This application is a divisional of U.S. application Ser. No. 15/743,869 filed Jan. 11, 2018, which is the National Phase of PCT International Application No. PCT/JP2016/073077, filed on Aug. 5, 2016, which claims priority under 35 U.S.C. § 119(a) to Patent Application No. 2015-158539, filed in Japan on Aug. 10, 2015, all of which are hereby expressly incorporated by reference into the present application.

REFERENCE TO ELECTRONIC SEQUENCE LISTING

This application contains a Sequence Listing which has been submitted electronically in .XML format and is hereby incorporated by reference in its entirety. Said .XML copy, created on Oct. 14, 2022, is named "PH-6650-PCT-US-DIVI Sequence Listing.xml" and is 86,123 bytes in size. The sequence listing contained in this .XML file is part of the specification and is hereby incorporated by reference herein in its entirety.

TECHNICAL FIELD

The present invention relates to a novel immune inducer useful as an active ingredient in an agent for treating or preventing cancer.

BACKGROUND ART

PDS5A (PDS5, regulator of cohesion maintenance, homolog A) protein, also known as SSC-112, is a protein identified as a cell cycle regulator involved in the distribution of chromosomes.

PDS5A protein has been suggested to be associated with the development of cancer. For example, Patent Literature 1 discloses that the expression of PDS5A protein is higher in nasopharyngeal cancer, renal cancer, liver cancer and one type of breast cancer cells as compared to normal tissue. Further, Patent Literature 1 also discloses that the proliferation of cancer cells can be inhibited by suppressing the expression of PDS5A protein in the cancer cells using an antisense nucleic acid, ribozyme or siRNA against PDS5A gene, or an anti-PDS5A protein antibody, and that it can induce apoptosis in cancer cells by administering the full-length PDS5A protein or a partial peptide of the protein.

Patent Literature 2 discloses that the PDS5A protein that bind to HLA-A0201, which is a subtype of MHC class I molecules, and partial peptides thereof have an immune-inducing activity against cancer cells, and thus are useful for treatment and/or prevention of cancer. However, Patent Literature 2 does not disclose all the peptides that bind to HLA-A0201, nor information on peptides that bind to sub-types other than HLA-A0201.

CITATION LIST

Patent Literature

Patent Literature 1: WO 2002/081641
Patent Literature 2: WO 2011/027807

SUMMARY OF INVENTION

Technical Problem

An object of the present invention is to find a novel polypeptide useful as an active ingredient in an agent for treating or preventing cancer, and to provide the use of the polypeptide as an immune inducer.

Another object of the present invention is to provide an isolated antigen-presenting cell including a complex of the polypeptide and an HLA molecule, and an isolated T cell which selectively binds to a complex of the polypeptide and an HLA molecule, as well as an agent for treating or preventing cancer including the same.

Solution to Problem

As a result of intensive research, the present inventors have found that the human PDS5A protein consisting of the amino acid sequence represented by SEQ ID NO: 2 is specifically expressed in tissues or cells of leukemia, malignant lymphoma, breast cancer, liver cancer, prostate cancer, pancreatic cancer, ovarian cancer, renal cancer, colorectal cancer, stomach cancer, malignant brain tumor, esophageal cancer, and lung cancer. Further, the inventors have found out that a partial peptide present in a specific region of the PDS5A protein has an ability (immune-inducing activity) to activate and propagate T cells specific to the polypeptide via the presentation by the antigen-presenting cells, and that the immune-inducing activity is useful for the treating or preventing cancer. Based on these findings, the inventors have found out that the polypeptide can be used as an active ingredient in an immune inducer for treating and/or preventing cancer, and that antigen-presenting cells which have been in contact with the peptide, and T cells which have been in contact with the antigen-presenting cells are also useful in the treatment or prevention of cancer, thereby completing the present invention.

Specifically, the present invention has the following characteristics (1) to (14).

(1) An immune inducer comprising, as an active ingredient, the following (i) or (ii):
(i) at least one polypeptide having an immune-inducing activity and selected from the group of polypeptides (a) or (b) below:
(a) polypeptides consisting of seven or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 and positions 1074 to 1215 in the amino acid sequence represented by SEQ ID NO: 2;
(b) polypeptides comprising one to several amino acid deletions, substitutions and/or additions in the amino acid sequence of any one of the polypeptides (a);
(ii) a recombinant vector comprising at least one polynucleotide encoding any one of the polypeptides, and capable of expressing the polypeptide in vivo.
(2) The immune inducer according to (1), wherein the polypeptide (i) binds to a MHC class I molecule.
(3) The immune inducer according to (2), wherein the polypeptide (i) is any one of the polypeptides selected from the group of polypeptides (c) to (e) below:

(c) polypeptides consisting of the amino acid sequences represented by SEQ ID NOs: 3 to 34;

(d) polypeptides comprising one to several amino acid deletions, substitutions and/or additions in the amino acid sequence of any one of the polypeptides (c);

(e) polypeptides each comprising as a partial sequence any one of the polypeptides (c) or (d).

(4) The immune inducer according to (1), wherein the polypeptide (i) binds to a MHC class II molecule.

(5) The immune inducer according to (4), wherein the polypeptide (i) is any one of the polypeptides selected from the group of polypeptides (f) to (h) below:

(f) polypeptides consisting of the amino acid sequences represented by SEQ ID NOs: 35 to 67;

(g) polypeptides comprising one to several amino acid deletions, substitutions and/or additions in the amino acid sequence of any one of the polypeptides (f);

(h) polypeptides each comprising as a partial sequence any one of the polypeptides (f) or (g).

(6) The immune inducer according to any one of (1) to (5), which is used as an active ingredient in an agent for treating or preventing cancer.

(7) The immune inducer according to (6), wherein the cancer is a cancer expressing PDS5A protein.

(8) The immune inducer according to any one of (6) or (7), wherein the cancer is leukemia, malignant lymphoma, prostate cancer, liver cancer, breast cancer, pancreatic cancer, ovarian cancer, renal cancer, colorectal cancer, stomach cancer, malignant brain tumor, lung cancer or esophageal cancer.

(9) The immune inducer, according to any one of (1) to (8), further comprising an immunopotentiator.

(10) A polypeptide having an immune-inducing activity and selected from the group of polypeptides (a) or (b) below:

(a) polypeptides having an immune-inducing activity and consisting of 7 or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 and positions 1074 to 1215 in the amino acid sequence represented by SEQ ID NO: 2;

(b) polypeptides comprising one to several amino acid deletions, substitutions and/or additions in the amino acid sequence of any one of the polypeptides (a).

(11) The polypeptide according to (10), wherein the polypeptide is any one polypeptide selected from the group of polypeptides (c) to (e) below:

(c) polypeptides consisting of the amino acid sequences represented by SEQ ID NOs: 3 to 34;

(d) polypeptides comprising one to several amino acid deletions, substitutions and/or additions in the amino acid sequence of any one of the polypeptides (c);

(e) polypeptides each comprising as a partial sequence any one of the polypeptides (c) or (d).

(12) The polypeptide according to (10), wherein the polypeptide is any one polypeptide selected from the group of polypeptides (f) to (h) below:

(f) polypeptides consisting of the amino acid sequences represented by SEQ ID NOs: 35 to 67;

(g) polypeptides comprising one to several amino acids deletions, substitutions and/or additions in the amino acid sequence of any one of the polypeptides (f);

(h) polypeptides each comprising as a partial sequence any one of the polypeptides (f) or (g).

(13) An isolated antigen-presenting cell comprising a complex of the polypeptide having an immune-inducing activity according to any one of (10) to (12) and a MHC molecule.

(14) An isolated T cell which selectively binds to a complex of the polypeptide having an immune-inducing activity according to any one of (10) to (12) and a MHC molecule.

The present specification encompasses the disclosure of Japanese Patent Application No. 2015-158539 to which the present application claims priority.

Effects of Invention

The present invention provides a novel immune inducer useful as an active ingredient in an agent for treating or preventing cancer.

Further, as specifically shown in Examples to be described later, the polypeptides used in the present invention can induce immune cells that kill cancer cells, thereby enabling the reduction in size or regression of an already existing cancer. In addition, the peptides used in the present invention can also enhance the induction of the immune cells that kill cancer cells, and thereby enabling the reduction in size or regression of an already existing cancer. Therefore, the polypeptides according to the present invention are useful as an active ingredient in an agent for treating or preventing cancer.

BRIEF DESCRIPTION OF DRAWINGS

In FIG. 2, Lanes 13 to 29 on the horizontal axis show the IFN-γ-producing abilities of HLA-A0201-positive CD8-positive T cells in response to stimulation by dendritic cells pulsed with the polypeptides having the amino acid sequences represented by SEQ ID NOs: 3 to 19, respectively. Lane 1 shows the result obtained when the above treatment was carried out without adding any polypeptide (Mock); Lane 2 shows the result obtained when the above treatment was carried out with the addition of a negative control polypeptide having the amino acid sequence represented by SEQ ID NO: 74, which is outside the scope of the present invention; Lane 3 shows the result obtained when the above treatment was carried out with the addition of the full-length PDS5A protein consisting of the amino acid sequence represented by SEQ ID NO: 2; and Lanes 4 to 12 show the results obtained when the above treatment was carried out with the addition of polypeptides having the amino acid sequences represented by SEQ ID NOs: 75 to 83, respectively, which are outside the scope of the present invention.

In FIG. 3, Lanes 4 to 18 on the horizontal axis show the IFN-γ-producing abilities of HLA-A24-positive CD8-positive T cells in response to stimulation by dendritic cells pulsed with the polypeptides having the amino acid sequences represented by SEQ ID NOs: 20 to 34, respectively. Lane 1 shows the result obtained when the above treatment was carried out without adding any polypeptide (Mock); Lane 2 shows the result obtained when the above treatment was carried out with the addition of a negative control peptide having the amino acid sequence represented by SEQ ID NO: 84, which is outside the scope of the present invention; and Lane 3 shows the result obtained when the above treatment was carried out with the addition of the full-length PDS5A protein consisting of the amino acid sequence represented by SEQ ID NO: 2.

In FIG. 4A, Lanes 13 to 29 on the horizontal axis show the cytotoxic activities, against U251 cells, of HLA-A0201-positive CD8-positive T cells induced using the polypeptides having the amino acid sequences represented by SEQ ID NOs: 3 to 19, respectively. Lane 1 shows the cytotoxic activity of CD8-positive T cells (Mock) induced without adding any polypeptide; Lane 2 shows the cytotoxic activity of CD8-positive T cells induced using the negative control polypeptide (SEQ ID NO: 74); Lane 3 shows the cytotoxic activity of CD8-positive T cells induced using the full-length PDS5A protein consisting of the amino acid sequence represented by SEQ ID NO: 2; and Lanes 4 to 12 show the cytotoxic activities of CD8-positive T cells induced using the polypeptides having the amino acid sequences represented by SEQ ID NOs: 75 to 83, respectively, which are outside the scope of the present invention.

In FIG. 4B, Lanes 12 to 28 on the horizontal axis show the cytotoxic activities, against Jurkat cells, of HLA-A0201-positive CD8-positive T cells induced using the polypeptides having the amino acid sequences represented by SEQ ID NOs: 3 to 19, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 74); Lane 3 shows the cytotoxic activity of the CD8-positive T cells induced using the full-length PDS5A protein consisting of the amino acid sequence represented by SEQ ID NO: 2; and Lanes 4 to 11 show the cytotoxic activities of CD8-positive T cells induced using the polypeptides having the amino acid sequences represented by SEQ ID NOs: 75 to 83, respectively, which are outside the scope of the present invention.

In FIG. 5A, Lanes 4 to 18 on the horizontal axis show the cytotoxic activities, against THP1 cells, of HLA-A24-positive CD8-positive T cells stimulated using the polypeptides having the amino acid sequences represented by SEQ ID NOs: 20 to 34, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 84); and Lane 3 shows the cytotoxic activity of the CD8-positive T cells induced using the PDS5A protein consisting of the amino acid sequence represented by SEQ ID NO: 2.

In FIG. 5B, Lanes 4 to 18 on the horizontal axis show the cytotoxic activities, against SW480 cells, of the HLA-A24-positive CD8-positive T cells stimulated using the polypeptides having the amino acid sequences represented by SEQ ID NOs: 20 to 34, respectively. Lane 1 shows the cytotoxic activity of CD8-positive T cells (Mock) induced without adding any polypeptide; Lane 2 shows the cytotoxic activity of the CD8-positive T cells induced using the negative control polypeptide (SEQ ID NO: 84); and Lane 3 shows the cytotoxic activity of the CD8-positive T cells induced using the PDS5A protein consisting of the amino acid sequence represented by SEQ ID NO: 2.

In FIG. 6, Lanes 4 to 36 on the horizontal axis show the IFN-γ-producing abilities of HLA-DRB1*04-positive CD4-positive T cells in response to stimulation by dendritic cells pulsed with the polypeptides having the amino acid sequences represented by SEQ ID NOs: 35 to 67, respectively. Lane 1 shows the result obtained when the above treatment was carried out without adding any polypeptide (Mock); Lane 2 shows the result obtained when the above treatment was carried out with the addition of a negative control polypeptide having the amino acid sequence represented by SEQ ID NO: 85, which is outside the scope of the present invention; and Lane 3 shows the result obtained when the above treatment was carried out with the addition of the full-length PDS5A protein consisting of the amino acid sequence represented by SEQ ID NO: 2.

DESCRIPTION OF EMBODIMENTS

<Polypeptide>

Figure 1:
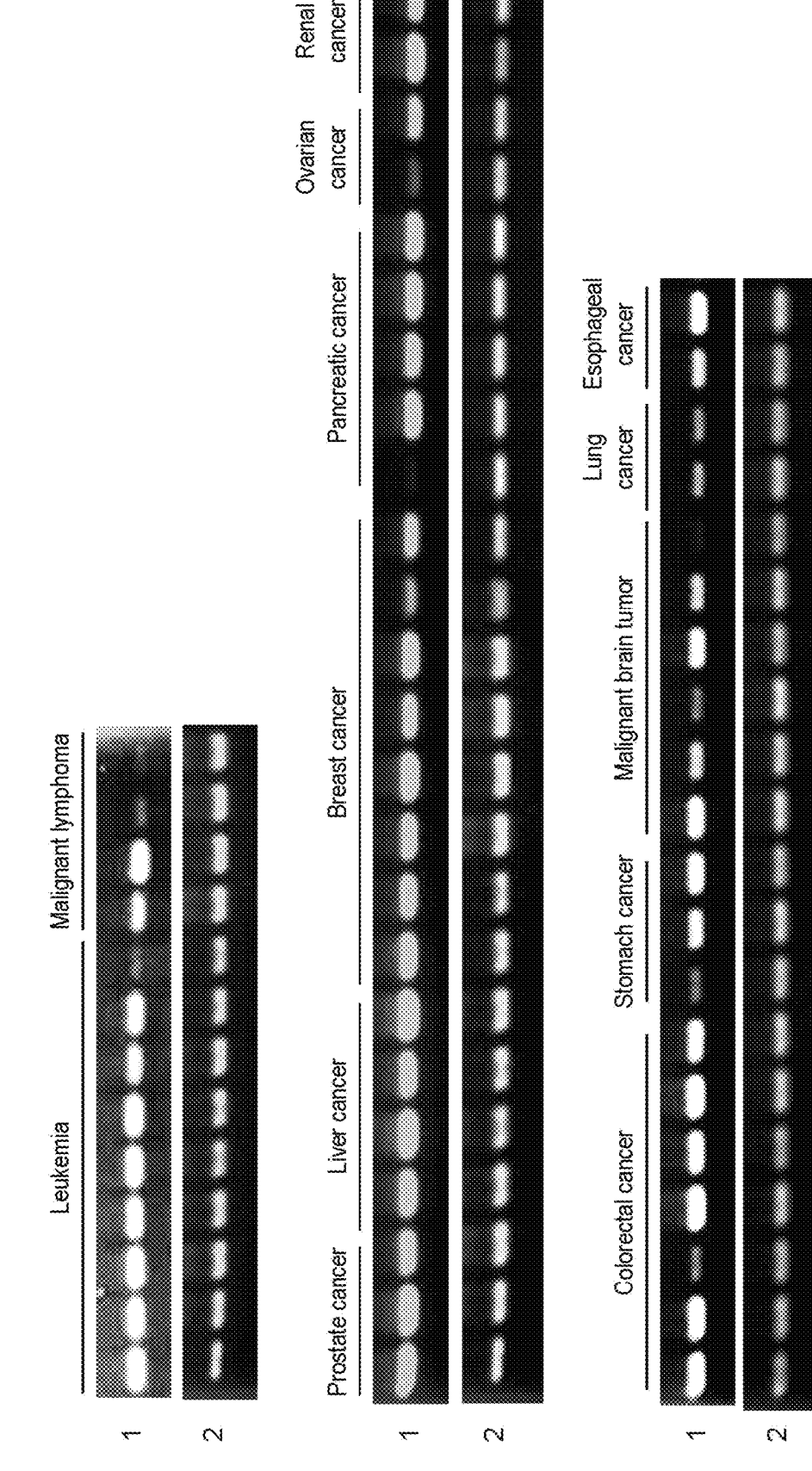
FIG. 1 shows the expression patterns of PDS5A gene, in human tumor tissues and cancer cell lines. Reference number 1 indicates the expression pattern of the human PDS5A gene. Reference number 2 indicates the expression pattern of human GAPDH gene, which is a human housekeeping gene.

In the present invention, the term "polypeptide" refers to a molecule formed by peptide bonding of a plurality of amino acids. The polypeptides according to the present invention include not only polypeptide molecules composed of a large number of amino acids but also low-molecular-weight molecules (oligopeptides) composed of a small number of amino acids.

The polypeptide constituting the immune inducer according to the present invention may be, for example, at least one polypeptide having an immune-inducing activity and selected from the group of polypeptides (a) or (b) below:

(a) polypeptides consisting of 7 or more consecutive amino acids within the region of positions 24 to 97 (74 amino acids), positions 113 to 132 (20 amino acids), positions 134 to 197 (64 amino acids), positions 204 to 225 (22 amino acids), positions 265 to 332 (68 amino acids), positions 378 to 463 (86 amino acids), positions 472 to 498 (27 amino acids), positions 533 to 567 (35 amino acids), positions 613 to 643 (31 amino acids), positions 671 to 735 (65 amino acids), positions 737 to 780 (44 amino acids), positions 792 to 830 (39 amino acids), positions 832 to 899 (68 amino acids), positions 920 to 943 (24 amino acids), positions 946 to 993 (58 amino acids), positions 1029 to 1069 (41 amino acids)

and positions 1074 to 1215 (142 amino acids) in the human PDS5A protein consisting of the amino acid sequence represented by SEQ ID NO: 2, when the initiator methionine is defined as position 1;

(b) polypeptides comprising one to several amino acid deletions, substitutions, and/or additions in the amino acid sequence of any one of the polypeptides (a).

In the present invention, the expression "consisting of an amino acid sequence" means that amino acid residues are arranged in a specific order. Therefore, for example, a "polypeptide consisting of the amino acid sequence represented by SEQ ID NO: 2" refers to a polypeptide which has the amino acid sequence of Met Asp Phe Thr . . . (omitted) . . . . Asp Leu Gln Arg represented by SEQ ID NO: 2, and which has a size of 1337 amino acid residues. Further, in the present specification, the "polypeptide consisting of the amino acid sequence represented by SEQ ID NO: 2" is often abbreviated as the "polypeptide of SEQ ID NO: 2", for example. The same applies for the expression "consisting of a base sequence".

The term "immune-inducing activity" as used in the present invention refers to an ability to activate and propagate T cells that respond to cancer cells expressing the PDS5A protein. Specifically, the immune-inducing activity means that: the IFN-γ-producing ability of cytotoxic T cells and/or helper T cells stimulated by the PDS5A protein or a partial polypeptide thereof is higher than that of non-stimulated control T cells; the cytotoxic activity against cancer cells expressing the PDS5A protein of the cytotoxic T cells stimulated by the PDS5A protein or a partial polypeptide thereof is higher than that of the non-stimulated control T cells; the cytotoxic activity of the helper T cells stimulated by the PDS5A protein or a partial polypeptide thereof is enhanced, as compared to that of the non-stimulated control T cells; or the cytotoxic T cells or helper T cells stimulated by the PDS5A protein or a partial polypeptide thereof proliferate more than that of the non-stimulated control T cells.

The proliferation of cells can be confirmed by: visual observation; cell counting under a microscope; flow cytometry; the amount of tritium thymidine in the medium incorporated into the cells; and the like. Further, the measurement of the IFN-γ-producing ability can be performed, for example, by the known ELISPOT assay, and the like. Specifically, as will be described in the Examples below, for example, T cells are first cocultured with a polypeptide whose immune-inducing activity is to be evaluated (the PDS5A protein or a partial polypeptide thereof in the present invention) and antigen-presenting cells derived from peripheral blood mononuclear cells (hereinafter, referred to as "PBMCs"), to allow T cells to be contacted with the antigen-presenting cells presenting the polypeptide to be evaluated. Subsequently, the amount of IFN-γ produced by the T cells is measured using an antibody specific to IFN-γ. This allows for measuring the number of immune cells in the T cells. The immune-inducing activity can then be evaluated based on the thus obtained measurement results.

The cytotoxic activity can be evaluated, for example, by coculturing T cells with a polypeptide whose cytotoxic activity is to be evaluated (the PDS5A protein or a partial polypeptide thereof in the present invention) and antigen-presenting cells derived from PBMCs, and then analyzing whether or not the T cells show an ability to suppress the proliferation of tumor cells or to kill tumor cells (hereinafter, referred to as "cytotoxic activity") in vitro. The contact between the T cells and the antigen-presenting cells can be achieved by coculturing both of the cells in a liquid medium, as will be describe later. The measurement of the cytotoxic activity can be carried out, for example, by a known method referred to as the ⁵¹Cr release assay, described in Int. J. Cancer, 58: P 317, 1994.

By administering the T cells induced as described above to a cancer-bearing living body, the size of tumor can be reduced or tumor can be regressed due to the cytotoxic activity of the T cells. Therefore, the above described immune-inducing activity can also be evaluated as an ability to suppress the proliferation of cancer cells, or as an ability to cause a reduction in size or the disappearance of a cancer tissue (tumor) (hereinafter, referred to as "anti-tumor activity").

In cases where the above described polypeptide is used for treatment or prevention of cancer, the evaluation of the immune-inducing activity is preferably carried out using the cytotoxic activity or the anti-tumor activity as an index, although the index is not particularly limited thereto.

Since a polypeptide of about 7 or more amino acid residues can include an epitope and such a polypeptide can exhibit antigenicity and immunogenicity, and can have an immune-inducing activity, as is well known in the art, and thus can be used as the immune inducer according to the present invention.

Accordingly, the polypeptide (a) is a polypeptide consisting of 7 or more consecutive amino acids, preferably 8, 9 or 10 or more consecutive amino acids, within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2; and having an immune-inducing activity. The polypeptide particularly preferably has the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2.

As a principle of immune induction by administration of a cancer antigen polypeptide, the polypeptide is incorporated into an antigen-presenting cell and then degraded into smaller fragments by peptidases in the cell, and subsequently, the fragments of the antigenic peptide are presented on the surface of the antigen-presenting cell. It is known that cytotoxic T cells and the like recognize antigens presented on the cell surface, and selectively kill cancer cells presenting the antigens on the cell surface. Further, it is also known that helper T cells recognize antigens presented on the surface of antigen-presenting cells, and enhance the induction of cytotoxic T cells that selectively kill cancer cells presenting the antigens on the on the cell surface. The size of the antigen polypeptide presented on the surface of the antigen-presenting cell is relatively small, and is about 7 to 30 amino acids. Therefore, in terms of allowing the polypeptide to be presented on antigen-presenting cells, the polypeptide (a) is preferably of about 7 to 30 consecutive amino acids, in the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2. A polypeptide consisting of about 8 to 30, about 9 to 30 or about 9 to 25 amino acids is sufficient. These relatively small polypeptides may be presented directly on the surface of the antigen-presenting cells without being incorporated into the cells.

Further, since the polypeptide incorporated into an antigen-presenting cell is cleaved at random sites by peptidases in the cell to yield various polypeptide fragments, and the resulting polypeptide fragments are then presented on the surface of the antigen-presenting cell, the administration of a large polypeptide, such as one having the amino acid sequence of positions 24 to 97, positions 113 to 132, positions 134 to 197, positions 204 to 225, positions 265 to 332, position 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2, inevitably leads to the production of polypeptide fragments active for immune induction via antigen-presenting cells, due to the degradation of the polypeptide in the antigen-presenting cells. Therefore, a large polypeptide can also be used for immunity induction via antigen-presenting cells. For example, a polypeptide consisting of 30 or more amino acids, preferably 40 or more, more preferably 50 or more, and still more preferably 100 or more amino acids may be used.

Further, the polypeptides according to the present invention can be checked with a checking medium, such as HLA Peptide Binding Predictions (bimas.dort.nih.gov/molbio/ hla_bind/index.htmL) in Bioinformatics & Molecular Analysis Selection (BIMAS), or SYFPEITHI, which can search epitope peptides consisting of from 8 to 25, preferably from 9 to 24, and more preferably from 9 to 23 amino acids and having binding motifs for class I molecules or class II molecules of MHC (HLA, in humans) to be described later, to carry out the screening of peptides which may be epitope peptides. Specifically, the above described polypeptide is a polypeptide consisting of 7 or more consecutive amino acids within the region of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2. Examples of the polypeptide include: polypeptides represented by SEQ ID NOs: 3 to 67; and polypeptides each comprising as a partial sequence any one of the polypeptides consisting of the amino acid sequences represented by SEQ ID NOs: 3 to 67, and having 10 to 30 amino acid residues. Among the polypeptides represented by SEQ ID NOs: 3 to 67, and the polypeptides each comprising as a partial sequence any one of the polypeptides consisting of the amino acid sequences represented by SEQ ID NOs: 3 to 67 and having 10 to 30 amino acid residues, the immune-inducing activity of the polypeptides represented by SEQ ID NOs: 3 to 67 is due to the binding to MHC class I molecules, and the immune-inducing activity of the polypeptides represented by SEQ ID NOs: 35 to 67 is due to the binding to MHC class II molecules.

On the other hand, the polypeptide (b) is a polypeptide comprising one or several amino acid substitutions, deletions and/or additions in the amino acid sequence of the polypeptide (a), and which has an immune-inducing activity. For example, the polypeptide (b) include a polypeptide comprising one or several amino acid substitutions, deletions and/or additions in the amino acid sequence represented by any one of SEQ ID NOs: 3 to 67.

The term "several" as used in the present invention refers to an integer of from 2 to 10, preferably an integer of from 2 to 6, more preferably an integer of 2 to 4, and still more preferably an integer of 2 or 3.

In general, it is thought that the modification of one or several amino acids in a polypeptide does not affect the functions of the original polypeptide; in some cases, such a modification is thought to even enhance a desired function of the original polypeptide. In fact, a modified peptide comprising one to several modifications (namely, substituted, deleted, added and/or inserted) in the amino acid sequence of the original amino acid sequence is known to retain the biological activity of the original peptide (Mark et al., 1984, Proc Natl Acad Sci USA, 81:5662-5666, Zoller and Smith, 1982, Nucleic Acids Res. 10:6487-6500, Dalbadie-McFarland et al., 1982, Proc Natl Acad Sci USA. 79:6409-6413). Accordingly, the polypeptide (b) also may exhibit an immune-inducing activity, and thus may be used for the preparation of the immune inducer according to the present invention.

The 20 types of amino acids constituting naturally-occurring proteins can be classified into groups of amino acids with similar properties, such as, for example: neutral amino acids with side chains having low polarity (Gly, Ile, Val, Leu, Ala, Met and Pro); neutral amino acids having hydrophilic side chains (Asn, Gln, Thr, Ser, Tyr and Cys); acidic amino acids (Asp and Glu), basic amino acids (Arg, Lys and His); and aromatic amino acids (Phe, Tyr and Trp). It is known, in many cases, that the substitutions of amino acids within the same group do not alter the properties of the polypeptide. Therefore, in cases where an amino acid residue(s) in the polypeptide (a) of the present invention is/are substituted, the substitution(s) is/are preferably carried out within the same group, because it increases the likelihood of retaining the immune-inducing activity.

Further, the polypeptide (b) may be a polypeptide which has a sequence identity of 90% or more, preferably 95% or more, more preferably 98% or more, and still more preferably 99% or more or 99.5% or more to the amino acid sequence of positions 24 to 97, positions 113 to 132, positions 134 to 197, positions 204 to 225, positions 265 to 332, positions 378 to 463, positions 472 to 498, positions 533 to 567, positions 613 to 643, positions 671 to 735, positions 737 to 780, positions 792 to 830, positions 832 to 899, positions 920 to 943, positions 946 to 993, positions 1029 to 1069 or positions 1074 to 1215 in the amino acid sequence represented by SEQ ID NO: 2, and which has an immune-inducing activity.

As used herein, the term "sequence identity" between amino acid sequences (or base sequences) refers to a percent value obtained by: aligning two amino acid sequences (or base sequences) to be compared such that the number of matched amino acid residues (or bases) between the amino acid sequences (or base sequences) is maximized; and dividing the number of matched amino acid residues (or the number of matched bases) by the total number of amino acid residues (or the total number of bases). When aligning sequences, a gap(s) is/are inserted into one or both of the two sequences to be compared, if required. Such alignment of sequences can be carried out using a known program such as BLAST, FASTA or CLUSTAL W. In cases where a gap(s)

is/are inserted, the above-described total number of amino acid residues is the number of residues obtained by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

When used in connection with treatment or prevention of cancer, the polypeptide according to the present invention should be expressed on the surface of a cell or an exosome, preferably as a complex of the peptide and any of various classes of HLA. Accordingly, it is preferred to select a peptide having not only an immune-inducing activity, but also a high binding affinity to various classes of HLA. For this purpose, the peptide may be modified by substitution, insertion, deletion and/or addition of its amino acid residue (s), to obtain a modified peptide having an improved binding affinity. Since the regularity of the sequences of the peptides presented via binding to various classes of HLA is known, in addition to the regularity of naturally presented peptides (J Immunol, 1994, 152:3913; Immunogenetics, 1995, 41:178; J Immunol, 1994, 155:4307), it is possible to introduce a modification based on such a regularity into the immunogenic peptide according to the present invention. For example, the substitution of the second amino acid from the N terminus with leucine or methionine, and/or the substitution of the amino acid at the C terminus with valine or leucine may be desirable for the purpose of improving the binding affinity to HLA-A24. Accordingly, a peptide having the amino acid sequence of any one of SEQ ID NOs: 20 to 34, in which the second amino acid from the N terminus is substituted with leucine or methionine, and/or the amino acid at the C terminus is substituted with valine or leucine, is also within the scope of the present invention.

Substitutions can be introduced not only at the terminal amino acids, but also at potential TCR recognition site(s) of peptides. Several studies have demonstrated that an amino acid-substituted peptide has the same or better properties as compared to the original peptide, and examples of the amino acid-substituted peptide include CAP1, p53 (264-272), Her-2/neu (369-377) and gp100 (209-217) (Zaremba et al. 1997, Cancer Res. 57:4570-4577, T. K. Hoffmann et al. 2002, J Immunol. 168 (3): 1338-47, S. O. Dionne et al. 2003, Cancer Immunol immunother. 52: 199-206, and S. O. Dionne et al. 2004, Cancer Immunology, Immunotherapy, 53: 307-314).

In addition to the above described modifications, it is also possible to link the polypeptide according to the present invention with another substance(s), as long as the resulting linked polypeptide retains the necessary immune-inducing activity of the original peptide. Examples of the other substance include but not limited to peptides, lipids, sugars and sugar chains, acetyl groups, and natural and synthetic polymers. The peptide can also include a modification such as glycosylation, side-chain oxidation or phosphorylation, provided that the biological activity of the original peptide is not impaired due to the modification. These types of modifications can be carried out to confer additional functions (such as targeting function and delivery function) to the polypeptide, or to stabilize the polypeptide. For example, it is known in the art to introduce a D-amino acid, an amino acid mimic or a non-natural amino acid into a polypeptide in order to enhance the in vivo stability thereof; and this concept can be utilized in the polypeptides according to the present invention. The stability of a polypeptide can be assayed by several methods. For example, the stability can be tested using peptidases as well as various types of biological media such as human plasma and serum (see, for example, Verhoef et al., 1986, Eur J Drug Metab Pharmacokin, 11:291-302).

Further, the polypeptide according to the present invention may be linked to another peptide(s) via a spacer(s) or a linker(s). Examples of the other peptide include but not limited to epitope peptides derived from other polypeptides. Alternatively, two or more polypeptides according to the present invention may be liked via a spacer(s) or a linker(s). The peptides to be linked via a spacer(s) or a linker(s) may be the same, or different from each other. The types of the spacer and the linker are not particularly limited, and examples thereof include those composed of peptides, more preferably, those composed of peptides having one or more cleavage sites that can be cleaved by enzymes such as peptidases, proteases and proteasomes. The linker or spacer may be, for example, AAY (P. M. Daftarian et al., J Trans Med, 2007, 5:26), AAA, NKRK (SEQ ID NO: 86) (R. P. M. Sutmuller et al., J Immunol. 2000, 165:7308-7315), or one to several lysine residues (S. Ota et al., 2002, Can Res. 62:1471-1476, K. S. Kawamura et al., 2002, J Immunol. 168:5709-5715), but not limited thereto. The present invention contemplates a polypeptide linked to another peptide(s) via a spacer(s) or a linker(s).

In cases where the polypeptides according to the present invention contain cysteine residues, these polypeptides tend to form dimers via disulfide bonds between the SH groups of the cysteine residues. Therefore, the dimers of these polypeptides are also included in the polypeptides according to the present invention.

The polypeptides according to the present invention can be prepared using known techniques. For example, the polypeptides can be synthesized by a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers.

In addition, the polypeptide of interest may be obtained using known genetic engineering techniques, by: preparing a polynucleotide encoding the above polypeptide; incorporating the polynucleotide into an expression vector; introducing the vector into a host cell; and then allowing the polypeptide of interest to be produced in the host cell. When obtaining the polypeptide of interest from the host cells, the polypeptide can be purified or isolated such that the polypeptide does not substantially include other naturally-occurring host cell proteins and fragments thereof, or other arbitrary chemical substances.

The polynucleotide encoding the above polypeptide can be easily prepared by a known genetic engineering technique or a conventional method using a commercially available nucleic acid synthesizer. For example, DNA having the base sequence of SEQ ID NO: 1 can be prepared by carrying out PCR using a human chromosomal DNA or cDNA library as a template, and a pair of primers designed to amplify the base sequence represented by SEQ ID NO: 1. The reaction conditions for the PCR can be set as appropriate, and examples thereof include but not limited to repeating a cycle consisting of reactions at: 94° C. for 30 seconds (denaturation), 55° C. for 30 seconds to 1 minute (annealing) and 72° C. for 2 minutes (extension), for 30 cycles, followed by a reaction at 72° C. for 1 minute. Further, the desired DNA can be isolated by preparing an appropriate probe(s) or primer(s) based on the information of the base sequence represented by SEQ ID NO: 1 and the amino acid sequence, and screening a cDNA library of human or the like using the probe(s) or primer(s). The cDNA library is preferably prepared from a cell, organ or tissue expressing the protein of SEQ ID NO: 2. The above described operations such as preparation of a probe(s) or primer(s), construction of a cDNA library, screening of a cDNA library and cloning of a gene of interest are known to those skilled in the art, and can be carried out according to the methods described, for example, in in Green, M. R. and Sambrook, J., 2012, Molecular Cloning: A Laboratory Manual Fourth Ed., Cold Spring Harbor Laboratory Press, Cold Spring Harbor, New York; Current Protocolin Molecular Biology: www.current-protocols.com; and the like. From the thus obtained DNA, DNA encoding the polypeptide (a) can be obtained. Further, since the codons encoding each amino acid are known, the base sequence of a polynucleotide encoding a specific amino acid sequence can be easily specified. Accordingly, the base sequence of a polynucleotide encoding the above described polypeptide (b) can also be easily specified, and thus, such a polynucleotide can also be synthesized using a commercially available nucleic acid synthesizer according to a conventional method.

The host cell may be any cell as long as it can express the above described polypeptide. Examples of prokaryotic cells include but not limited to *E. coli*; and Examples of eukaryotic cells include but not limited to mammalian cultured cells including monkey kidney cells COS-1 and Chinese hamster ovary cells CHO; budding yeast; fission yeast; silkworm cells; and *Xenopus laevis* egg cells.

In cases where a prokaryotic cell is used as the host cell, an expression vector containing an origin that enables its replication in a prokaryotic cell, a promoter, a ribosome binding site, a DNA cloning site a terminator etc. is used. Examples of the expression vector for *E. coli* include the pUC system, pBluescript II, pET expression system and pGEX expression system. The polypeptide encoded by the DNA can be expressed in the prokaryotic host cell by incorporating a DNA encoding the above polypeptide into such an expression vector, transforming a prokaryotic host cell with such a vector, and then culturing the resulting transformant. In this process, the polypeptide can also be expressed as a fusion protein with another protein.

In cases where a eukaryotic cell is used as the host cell, an expression vector for eukaryotic cells containing a promoter, a splicing site, poly(A) addition site, etc. is used. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, the polypeptide encoded by the DNA can be expressed in the eukaryotic host cell by incorporating a DNA encoding the above polypeptide into such an expression vector, transforming a eukaryotic host cell with such a vector, and then culturing the resulting transformant. In cases where pIND/V5-His, pFLAG-CMV-2, pEGFP-N1, pEGFP-C1 or the like is used as the expression vector, the above polypeptide can be expressed as a fusion protein to which any of various types of tags, such as His tag, FLAG tag, myc tag, HA tag and GFP, is added.

The introduction of the expression vector into the host cell can be carried out by a known method such as electroporation, the calcium phosphate method, the liposome method or the DEAE dextran method.

The polypeptide of interest can be isolated and purified from the host cells by a combination of known separation operations. Examples of the known separation operations include but not limited to: treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those in the form of a fusion protein with another arbitrary protein. Examples thereof include fusion proteins with glutathione S-transferase (GST) and fusion proteins with a His tag. Accordingly, such a polypeptide in the form of a fusion protein is also included within the scope of the present invention. Further, a polypeptide expressed in the transformed cell may be modified post-translationally in various ways. Such a post-translationally modified polypeptide is also included within the scope of the present invention, as long as it has an immune-inducing activity. Examples of such a post-translational modification include: elimination of N-terminal methionine; N-terminal acetylation; glycosylation; limited degradation by an intracellular protease; myristoylation; isoprenylation and phosphorylation.

<Immune Inducer>

An already existing tumor can be regressed by administering the polypeptide having an immune-inducing activity according to the present invention, or an expression vector containing the gene encoding the polypeptide, to a cancer-bearing living body. Further, the occurrence of a tumor can be prevented by administering the above described polypeptide having an immune-inducing activity or the gene encoding the polypeptide to a living body before the onset of cancer. Accordingly, the polypeptide according to the present invention or the gene encoding the polypeptide may be used as an active ingredient in immune inducer.

The terms "tumor" and "cancer" are each used herein to refer to a malignant neoplasia, and are used interchangeably. In this case, the cancer to be treated is preferably a cancer expressing the PDS5A protein, and more preferably leukemia, malignant lymphoma, prostate cancer, liver cancer, breast cancer, pancreatic cancer, ovarian cancer, renal cancer, colorectal cancer, stomach cancer, malignant brain tumor, lung cancer or esophageal cancer.

The subject animal is preferably a mammal, more preferably a mammal such as a primate, a pet animal, a domestic animal or a sport animal, still more preferably a human, a dog or a cat, and particularly preferably a human.

The cancer-affected individual (a cancer patient, in cases where the individual is a human) to be treated is preferably a cancer-affected individual whose cancer cells express the PDS5A protein in vivo. Specifically, preferred is a cancer-affected individual screened by the method of detecting cancer described in WO 2011/027807. In particular, the cancer-affected individual is preferably one screened by the fact that the expression levels of antibodies against the PDS5A protein contained in the sample obtained from the subject living body are higher as compared to the expression levels of the antibodies contained the sample obtained from a healthy individual. Examples of the sample to be used for screening of cancer-affected individuals to be treated include body fluids such as blood, serum, plasma, ascites and pleural effusion; tissues; and cells. In cases where the screening is carried out by measuring the expression levels of antibodies against the PDS5A protein, the sample is preferably serum, plasma, ascites or pleural effusion.

The administration of the immune inducer according to the present invention may be carried out either orally or parenterally. However, preferred administration routes are parenteral administrations such as intramuscular administration, subcutaneous administration, intravenous administration and intraarterial administration. In cases where the immune inducer is used for treatment of cancer, it can be administered to a regional lymph node in the vicinity of the tumor to be treated, in order to enhance its anti-cancer activity. The immune inducer can be administered in any dosage amount effective for inducing immunity. For example, in cases where the immune inducer is used for treatment or prevention of cancer, the agent may be administered in an amount effective for treatment or prevention of cancer. The amount effective for treatment or prevention of cancer can be selected as appropriate depending on the size of the tumor, symptoms, body weight and volume of the subject animal, and the like. In cases where the subject animal is a human, the effective amount is usually from 0.0001 to 1,000 μg, and preferably from 0.001 to 1,000 μg per day. The above described dosage amount can be administered in a single dose, or in several divided doses. It is preferred that the above dosage amount be divided and administered several times per day, and that the administration thereof be carried out every several days or several months. As will be specifically described in the Examples below, the immune inducer according to the present invention can regress an already formed tumor. Thus, since the immune inducer can exert its anti-cancer activity also against a small number of cancer cells in the early stages, the development or recurrence of cancer can be prevented by using the agent before the onset or after the treatment of the cancer. In other words, the immune inducer according to the present invention is useful in both the treatment and prevention of cancer, and can be used as an active ingredient in an agent for treating or preventing cancer.

The immune inducer according to the present invention contains as an active ingredient the above described polypeptide according to the present invention, and may consist of a single polypeptide, or of a combination of a plurality of polypeptides. By combining a plurality of the polypeptides according to the present invention, the immunity-inducing activity (activity to induce and activate cytotoxic T cells) of each of the polypeptides is enhanced, and a more efficient treatment or prevention of cancer may be achieved.

The immune inducer according to the present invention can also be used in combination with a known peptide(s) capable of inducing cytotoxic T cells. By combining the polypeptide(s) according to the present invention with such a known peptide(s), the immunity-inducing activity (activity to induce and activate cytotoxic T cells) of each of the polypeptides is enhanced, and a more efficient treatment or prevention of cancer may be achieved. The term "combination" as used in this case includes the case in which the immune inducer according to the present invention and a known peptide(s) capable of inducing cytotoxic T cells are administered separately or simultaneously. The expression "to be administered separately" as used herein means that the immune inducer according to the present invention and a known peptide(s) capable of inducing cytotoxic T cells are administered separately at different time points with a certain time interval therebetween. The order of administration is not limited. On the other hand, the expression "to be administered simultaneously" means that the immune inducer according to the present invention and a known peptide(s) capable of inducing cytotoxic T cells are mixed in advance and administered in the form of a mixture, or that the immune inducer according to the present invention and a known peptide(s) capable of inducing cytotoxic T cells are administered in separate forms but at the same time without any time interval.

The immune inducer according to the present invention can be used in combination with another immunopotentiator capable of enhancing the immune response in vivo. The other immunopotentiator may be included in the immune inducer according to the present invention, or may be administered to a patient as a separate composition, in combination with the administration of the immune inducer according to the present invention.

The "other immunopotentiator" includes, for example, an adjuvant. An adjuvant can enhance the immune response by providing an antigen reservoir (extracellularly or within macrophages), activate macrophages and stimulate specific sets of lymphocytes, so as to enhance the anti-cancer activity. Therefore, in cases where the immune inducer according to the present invention is used as an active ingredient in an agent for treating or preventing cancer, it is preferred that the immune inducer further contain an adjuvant, in addition to the polypeptide according to the present invention as an active ingredient. Many types of adjuvants are known in the art, and any of these adjuvants can be used. Specific examples of the adjuvants include MPL (SmithKline Beecham), analogs of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO 96/33739 (SmithKline Beecham); QS-7, QS-17, QS-18 and QS-L1 (So, H. S., et al., "Molecules and cells", 1997, 7:178-186); Freund's incomplete adjuvant; Freund's complete adjuvant; vitamin E; Montanide; alum; CpG oligonucleotides (see, for example, Kreig, A. M., et al., 1995, Nature 374: 546-549); poly-I:C and derivatives thereof (such as poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio of the above-described adjuvant to the polypeptide is typically from about 1:10 to 10:1, preferably from about 1:5 to 5:1, and more preferably about 1:1. However, the adjuvant is not limited to the above-described examples, and any adjuvant known in the art other than those described above can also be used, when administering the immune inducer according to the present invention (see, for example, Goding, "Monoclonal Antibodies: Principles and Practice", 2nd edition, 1986). Methods for preparing a mixture or an emulsion of an immune inducer and an adjuvant are well-known to those skilled in the art of vaccination.

Further, in addition to the above-described adjuvants, factors that stimulate the immune response of the subject may be used as the other immunopotentiator. For example, any of various types of cytokines having a property to stimulate lymphocytes and/or antigen-presenting cells can be used as the immunopotentiator in combination with the immune inducer according to the present invention. A number of such cytokines capable of enhancing the immune response are known to those skilled in the art, and examples thereof include but not limited to interleukin-12 (IL-12), GM-CSF, IL-18, interferon-α (IFN-α), interferon-β (IFN-β), interferon-ω (IFN-ω), interferon-γ (IFN-γ), and Flt3 ligand, which have been shown to enhance the protective action of vaccines. Any of such factors can also be used as the above-described immunopotentiator, and can be administered to a patient in combination with the immune inducer according to the present invention, either by being incorporated into the immune inducer according to the present invention, or as a separate composition.

<Agent for Treating or Preventing Cancer>

The immune inducer according to the present invention can be used as an active ingredient in an agent for treating or preventing cancer.

The agent for treating or preventing cancer can be formulated by mixing, as appropriate, the immune inducer according to the present invention with an additive(s) such as a pharmaceutically acceptable carrier, diluent and/or excipient suitable for each dosage form.

Formulation methods and additives which can be used are well-known in the art of pharmaceutical formulation, and any of the methods and additives can be used. Specific examples of the additives include but not limited to: diluents such as physiological buffer solutions; excipients such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the dosage form include oral preparations such as tablets, capsules, granules, powders and syrups; and parenteral preparations such as inhalants, injection solutions, suppositories and solutions. These formulations can be prepared by commonly known production methods.

<Antigen-Presenting Cells>

The polypeptide can be presented by the antigen-presenting cells by bringing the above described polypeptide into contact with antigen-presenting cells in vitro. In other words, the above described polypeptide (a) or (b) can be used as an agent for treating antigen-presenting cells. As the antigen-presenting cells, dendritic cells or B cells having MHC class I molecules and class II molecules can be preferably used. A variety of MHC class I molecules and class II molecules have been identified and are well known. MHC molecules in humans are referred to as HLA.

Examples of HLA class I molecules include HLA-A, HLA-B and HLA-C. More specific examples of HLA class I molecules include HLA-A, HLA-B and HLA-C; and still more specific examples thereof include HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

Examples of HLA class II molecules include HLA-DR, HLA-DQ and HLA-DP; and more specific examples thereof include HLA-DRB1*01, HLA-DRB1*03, HLA-DRB1*04, HLA-DRB1*0405, HLA-DRB1*07, HLA-DRB1*08, HLA-DRB1*11, HLA-DRB1*13, HLA-DRB1*15, HLA-DRB1*15, HLA-DQA1, HLA-DQB1 and HLA-DPB1.

The dendritic cells or B cells having HLA class I or HLA class II molecules can be prepared from blood or the like by a well-known method. For example, tumor specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

An immune response desirable for treating cancer may be induced by administering an effective amount of the thus obtained dendritic cells. The cells to be used can be obtained from bone marrow or umbilical cord blood provided by a healthy individual, or bone marrow or peripheral blood or the like of the patient himself. The use of autologous cells obtained from the patient himself is preferred, because they are highly safe and serious side effects are expected to be avoided. The peripheral blood or bone marrow may be any of a fresh sample, a cold-stored sample and a frozen sample. The peripheral blood may be obtained by culturing whole blood, or by culturing separated leukocyte components alone, and the latter is more efficient and thus preferred. Further, mononuclear cells may be separated among the leukocyte components. In cases where the cells to be used are those derived from bone marrow or umbilical cord blood, all the cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are derived, as well as CD4-positive cells and the like. There is no particular limitation on the method for producing the cytokines to be used, and any cytokine, either natural or recombinant, can be used as long as its safety and physiological activity have been confirmed. It is preferred to use a preparation with assured quality for medical use, in a minimum amount necessary. The concentration of the cytokine(s) to be added is not particularly limited as long as it can induce dendritic cells. In general, the total concentration of the cytokine(s) is preferably from about 10 to 1,000 ng/mL, and more preferably from about 20 to 500 ng/ml. The culture can be carried out using a well-known medium commonly used for culturing leukocytes. The temperature for cultivation is not particularly limited as long as it can propagate the leukocytes; however a temperature of about 37° C., which is the human body temperature, is most preferred. Further, the atmospheric environment during the culture is not particularly limited as long as it can propagate the leukocytes; however it is preferred that 5% $CO_2$ is allowed to flow. The period of time for cultivation is not particularly limited as long as a required number of cells can be induced within the period. The culture is usually carried out for a period of from 3 days to 2 weeks. The apparatuses used for separation and culture of the cells can be selected as appropriate. Preferred are apparatuses whose safety for medical use has been confirmed, and which can be operated stably and simply. As for the cell culturing apparatus, in particular, it is possible to use, not only a common vessel such as a Petri dish, flask or bottle, but also a multi-layer vessel, a multi-stage vessel, a roller bottle, a spinner bottle, a bag-type culture vessel, a hollow fiber column or the like.

The process for bringing the above-described polypeptide into contact with the antigen-presenting cells in vitro can be carried out by a well-known method. For example, it can be achieved by culturing the antigen-presenting cells in a culture medium containing the above described polypeptide. The concentration of the peptide in the medium is not particularly limited, and it is usually from about 1 to 100 μg/mL, and preferably from about 5 to 20 μg/mL. The cell density during the culture is not particularly limited, and it is usually from about $10^3$ to $10^7$ cells/mL, and preferably from about $5×10^4$ to $5×10^6$ cells/mL. The culture is preferably carried out at 37° C. under an atmosphere of 5% $CO_2$, according to a conventional method. The maximum length of the peptide which can be presented on the surface of the antigen-presenting cells is usually a length of about 30 amino acid residues. Therefore, in cases where the antigen-presenting cells are brought into contact with the polypeptide in vitro, the polypeptide may be prepared such that its length is not more than about 30 amino acid residues, but not particularly limited thereto.

By culturing the antigen-presenting cells with the above described polypeptide, the polypeptide is incorporated into MHC molecules of the antigen-presenting cells, and presented on the surface of the antigen-presenting cells. Thus, isolated antigen-presenting cells containing the complex of the polypeptide and the MHC molecule may be prepared using the above described polypeptide. Such antigen-presenting cells can present the polypeptide to T cells in vivo or in vitro, induce cytotoxic T cells or helper T cells specific to the polypeptide, and propagate these cells.

By bringing the thus prepared antigen-presenting cells containing the complex of the above described polypeptide and the MHC molecule, into contact with T cells, in vitro, it is possible to induce cytotoxic T cells or helper T cells specific to the polypeptide, and to allow the proliferation of these cells. This can be achieved by coculturing the antigen-presenting cells and T cells in a liquid medium. For example, it can be carried out by suspending the antigen-presenting cells in a liquid medium, placing the resulting suspension in a vessel, such as in wells of a microplate, adding T cells thereto, and then culturing the cells. The mixing ratio of the antigen-presenting cells to the T cells when coculturing these cells is not particularly limited, and is usually from about 1:1 to 1:100, and preferably from about 1:5 to 1:20 in terms of the number of the cells. The density of the antigen-presenting cells to be suspended in the liquid medium is not particularly limited, and it is usually from about 100 to 10 million cells/ml, and preferably from about 10,000 to 1 million cells/ml. Coculture is preferably carried out at 37° C. under an atmosphere of 5% $CO_2$, according to a conventional method. The period of time for culturing is not particularly limited, and it is usually from about 2 days to 3 weeks, and preferably from about 4 days to 2 weeks. Further, coculture is preferably carried out in the presence of one or more types of interleukins such as IL-2, IL-6, IL-7 and/or IL-12. In such cases, the concentration of IL-2 or IL-7 is usually from about 5 to 20 U/mL, the concentration of IL-6 is usually from about 500 to 2000 U/mL, and the concentration of IL-12 is usually from about 5 to 20 ng/ml, but not limited thereto. The above described coculture may be repeated once or several times, adding fresh antigen-presenting cells. For example, the operation of discarding the culture supernatant after the coculture and adding a fresh suspension of the antigen-presenting cells to further carrying out the coculture, may be repeated once or several times. The conditions for each coculture may be the same as described above.

The above described coculture allows for the induction and proliferation of cytotoxic T cells and helper T cells specific to the polypeptide. Thus, isolated T cells which selectively bind to the complex of the polypeptide and the MHC molecule may be prepared with the use of the above described polypeptide.

As will be described in the Examples below, the gene (PDS5A gene) encoding the PDS5A protein is expressed specifically in each of: leukemia leukocytes, malignant lymphoma tissues, malignant lymphoma cells, prostate cancer tissues, prostate cancer cells, liver cancer tissues, liver cancer cells, breast cancer tissues, breast cancer cells, pancreatic cancer tissues, pancreatic cancer cells, ovarian cancer tissues, ovarian cancer cells, renal cancer tissues, renal cancer cells, colorectal cancer tissues, colorectal cancer cells, stomach cancer tissues, stomach cancer cells, malignant brain tumor tissues, malignant brain tumor cells, lung cancer tissues, lung cancer cells, esophageal cancer tissues and esophageal cancer cells. Therefore, a significantly higher amount of the PDS5A protein is thought to be present in the cells of these cancer types, than in normal cells. When cytotoxic T cells or helper T cells prepared as described above are administered to a living body, while a part of the PDS5A protein present in cancer cells is presented by MHC molecules on the surface of the cancer cells, the thus presented protein serves as a marker to allow the cytotoxic T cells to damage the cancer cells, or enhance the cytotoxic activity of the cytotoxic T cells. Since antigen-presenting cells presenting the above described polypeptide can induce, and propagate cytotoxic T cells and helper T cells specific to the polypeptide, also in vivo, the administration of the antigen-presenting cells to a living body can also allow the cytotoxic T cells to damage the cancer cells, or enhance the cytotoxic activity of the cytotoxic T cells. In other words, the cytotoxic T cells and helper T cells as well as the antigen-presenting cells prepared using the above polypeptide are also useful as agents for treating or preventing cancer, as is the immune inducer according to the present invention.

In the case of administering the above described isolated antigen-presenting cells or isolated T cells to a living body, these cells are preferably prepared by treating antigen-presenting cells or T cells collected from the patient to be treated, with the polypeptide (a) or (b) as described above, in order to avoid the immune response in the living body, that attacks these cells as foreign substances.

The agent for treating or preventing cancer comprising as an active ingredient the antigen-presenting cells or isolated T cells is preferably administered via a parenteral administration route such as intravenous or intraarterial administration. The dosage amount is selected as appropriate depending on the symptoms, the purpose of administration and the like. The dosage amount is usually from one to 10 trillion cells, and preferably from 1 million to 1 billion cells, which amount is preferably administered once in several days or several months. The formulation may be, for example a suspension of the cells in physiological buffered saline, and the formulation may be used in combination with another anti-cancer agent(s), cytokine(s) and/or the like. Further, one, or two or more additives known in the field of pharmaceutical formulation can also be added to the formulation.

<Gene Vaccine>

Immune induction, namely, the induction of antibody production or cytotoxic T cells in the body of a subject animal, can also be achieved by allowing a polynucleotide encoding the polypeptide (a) or (b) to be expressed in the living body. This provides an effect equivalent to that provided by administering the polypeptide. In other words, the immune inducer according to the present invention may comprise as an active ingredient a recombinant vector which contains the polynucleotide encoding the above described polypeptide (a) or (b) and which can express the polypeptide in a living body. Such a recombinant vector capable of expressing an antigen polypeptide, which will be shown in the Examples below, is also referred to as a "gene vaccine".

The vector to be used for the production of a gene vaccine is not particularly limited as long as it can express a polypeptide in a cell of the subject animal (preferably, in a mammalian cell). The vector may be either a plasmid vector or a virus vector, and any vector known in the field of gene vaccines may be used. The polynucleotide, such as DNA or RNA, encoding the above described polypeptide can be easily prepared as described above, by a conventional method. Further, the polynucleotide may be incorporated into a vector using a method well-known to those skilled in the art.

The gene vaccine is preferably administered by a parenteral administration route, such as intramuscular, subcutaneous, intravenous or intraarterial administration. The dosage amount of the gene vaccine can be selected as appropriate depending on the type of the antigen and the like, and it is usually from about 0.1 μg to 100 mg, and preferably from about 1 µg to 10 mg, in terms of the weight of the gene vaccine per 1 kg of body weight.

The method utilizing a virus vector may be, for example, a method in which a polynucleotide encoding the above described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. In particular, a method utilizing a retrovirus, adenovirus, adeno-associated virus, vaccinia virus or the like is particularly preferred.

Examples of other methods include a method in which an expression plasmid is directly administered intramuscularly (DNA vaccine method), the liposome method, lipofectin method, microinjection method, calcium phosphate method and electroporation method. Of these, the DNA vaccine method and liposome method are particularly preferred.

Methods for allowing the gene encoding the polypeptide used in the present invention to actually act as a pharmaceutical include: an in vivo method comprising directly introducing the gene into the body of a subject; and an ex vivo method comprising collecting a certain type of cells from a subject animal, and introducing the gene into the cells ex vivo, followed by returning the cells to the body of the subject animal. Of these, the in vivo method is more preferred.

In cases where the gene is administered by the in vivo method, the gene may be administered through an appropriate administration route depending on the disease to be treated, symptoms and the like. For example, the gene can be administered by an intravenous, intraarterial, subcutaneous, intramuscular administration or the like. In the case of administering the gene by the in vivo method, the gene may be formulated into a dosage form such as a solution; but generally formulated as an injection solution or the like containing DNA encoding the above described peptide according to the present invention as an active ingredient. A commonly used carrier(s) may be added thereto if required. In the case of using a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence represented by SEQ ID NO:1" includes not only the base sequence actually represented by SEQ ID NO: 1, but also the sequence complementary thereto. Thus, "a polynucleotide having the base sequence represented by SEQ ID NO:1" includes a single-stranded polynucleotide having the base sequence actually represented by SEQ ID NO:1, a single-stranded polynucleotide having the base sequence complementary thereto, and a double-stranded polynucleotide consisting of these single-stranded polynucleotides. When the polynucleotide encoding the polypeptide used in the present invention is prepared, any one of these base sequences is to be selected as appropriate, which selection can be easily carried out by those skilled in the art.

EXAMPLES

The present invention will be more specifically described below, by way of Examples.

Example 1: Analysis of Expression in Various Tissues (1) Analysis of PDS5A Gene Expression in Various Cancer Cell Lines The gene sequence (SEQ ID NO: 1) encoding the amino acid sequence of human PDS5A protein is obtained from Gene Bank. The expression of the thus obtained gene in various types of human cell lines was analyzed by RT-PCR (Reverse Transcription-PCR). The reverse transcription reaction was carried out as follows. Specifically, from 50 to 100 mg of each tissue or 5 to $10\times10^6$ cells of each cell line, total RNA was extracted using TRIZOL reagent (manufactured by Life Technologies, Inc.) according to the protocol described in the attached instructions. The thus obtained total RNA was used to synthesize cDNA, using Superscript First-Strand Synthesis System for RT-PCR (manufactured by Life Technologies, Inc.) according to the protocol described in the attached instructions. As the cDNAs of normal human tissues (brain, hippocampus, testis, colon and placenta), Gene Pool cDNA (manufactured by Life Technologies, Inc.), QUICK-Clone CDNA (manufactured by Clontech Laboratories, Inc.) and Large-Insert cDNA Library (manufactured by Clontech Laboratories, Inc.) were used. The PCR reaction was carried out as follows, using primers specific to the obtained gene (the base sequences of the primes are represented by SEQ ID NOs: 68 and 69). Specifically, reagents and an attached buffer were added to prepare a mixture having a total volume of 25 µL, and containing 0.25 µL of a sample prepared by the reverse transcription reaction, 2 µM each of the above described primers, 0.2 mM each of dNTPs, and 0.65 U of ExTaq polymerase (manufactured by Takara Shuzo Co., Ltd.). The reaction was then carried out using Thermal Cycler (manufactured by Bio-Rad laboratories Inc.) by repeating a cycle consisting of reactions at 94° C. for 30 seconds, 55° C. for 30 seconds and 72° C. for 1 minute, for 30 times. At the same time, primers specific to GAPDH, which is a housekeeping gene (the base sequences of human GAPDH primers are represented by SEQ ID NOs: 70 and 71) were used as a control for comparison.

As a result, as shown in FIG. 1, the expression of the human PDS5A gene was detected in most of the cancer cell lines, namely, in the cell lines of leukemia, malignant lymphoma, prostate cancer, liver cancer, breast cancer, pancreatic cancer, ovarian cancer, renal cancer, colorectal cancer, stomach cancer, malignant brain tumor, lung cancer and esophageal cancer.

(2) Expression of PDS5A Protein in Human Cancer Tissue (Immunohistochemical Staining)

Immunohistochemical staining was carried out on 72 cancer tissue specimens in a paraffin-embedded multiple cancer tissue array (manufactured by Biomax Inc.). The human cancer tissue array was treated at 60° C. for 3 hours, and placed in a staining jar filled with xylene, and the operation of replacing xylene with a fresh one every 5 minutes was repeated 3 times. Subsequently, the same operation was carried out using ethanol and PBS-T instead of xylene. The human cancer tissue array was placed in a staining jar filled with a 10 mM citrate buffer solution (pH 6.0) containing 0.05% Tween 20, treated at 125° C. for 5 minutes, and then left to stand at room temperature for 40 minutes or more. Excess moisture around the tissue sections was wiped off with Kimwipes, the tissue sections were encircled using a DAKOPEN, and an adequate amount of Peroxidase Block (manufactured by DAKO) was added dropwise thereto. After allowing the array to stand at room temperature for 5 minutes, the array was placed in a staining jar filled with PBS-T, and the operation of replacing PBS-T with a fresh one every 5 minutes was repeated 3 times. A PBS-T solution containing 10% FBS, as a blocking solution, was applied to the array, and the array was left to stand in a moist chamber at room temperature for 1 hour. Subsequently, a commercially available rabbit polyclonal antibody (manufactured by Sigma-Aldrich Co. LLC.) which reacts to the PDS5A protein was diluted with a PBS-T solution containing 5% FBS to a concentration of 10 μg/mL, and the resulting solution was applied to the array, followed by allowing the array to stand overnight in a moist chamber controlled at 4° C. After washing the array with PBS-T for 10 minutes, for 3 times, an adequate amount of Peroxidase Labelled Polymer Conjugated (manufactured by DAKO) was added dropwise thereto, and the array was left to stand in a moist chamber at room temperature for 30 minutes. After washing the array with PBS-T for 10 minutes, for 3 times, a DAB color-developing solution (manufactured by DAKO) was applied thereto, and the array was left to stand at room temperature for about 10 minutes. Thereafter, the color-developing solution was discarded, and the array was washed with PBS-T for 10 minutes, for 3 times, followed by rinsing with distilled water. The array was then successively dipped in 70%, 80%, 90%, 95% and 100% ethanol solutions for 1 minute each, and then left to stand overnight immersed in xylene. The glass slide of the array was recovered, mounted with Glycergel Mounting Medium (manufactured by DAKO), and then observed.

As a result, strong expression of PDS5A protein was observed in most of the tissues of the cancers tested, namely: prostate cancer, liver cancer, breast cancer, pancreatic cancer, ovarian cancer, renal cancer, colorectal cancer, stomach cancer, malignant brain tumor, lung cancer and esophageal cancer.

Example 2: Induction of Peptide Epitope-Reactive CD8-Positive T Cells

(1) Prediction of Peptide Motifs which Bind to HLA-A0201 and HLA-A24

Information on the amino acid sequence of the human PDS5A protein represented by SEQ ID NO: 2 was obtained from GenBank. For the prediction of HLA-A0201 and HLA-A24 binding motifs, the amino acid sequence of the human PDS5A protein was analyzed with a computer-based prediction program using a known BIMAS software (available at bimas.dort.nih.gov/molbio/hla_bind). As a result, 17 types of polypeptides consisting of the amino acid sequences represented by SEQ ID NOs: 3 to 19, which were expected to be capable of binding to the HLA-A0201 molecule; and 14 types of polypeptides consisting of the amino acid sequences represented by SEQ ID NOs: 20 to 34, which were expected to be capable of binding to the HLA-A24 molecule; were selected. All the selected polypeptides were synthesized by Greiner Japan Co. Ltd. that provides custom peptide synthesis services. The quality of the synthesized polypeptides has been guaranteed by HPLC analysis and mass spectrometry.

(2) Induction of Peptide Epitope-Reactive CD8-Positive T Cells

Peripheral blood was separated from the blood of an HLA-A0201-positive healthy individual. The peripheral blood was layered on Lymphocyte separation medium (Organon Teknika Corporation, Durham, NC), and then centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for the preparation of dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1B (10 ng/ml, manufactured by Genzyme Corporation) and TNF-α (10 ng/ml, manufactured by Genzyme Corporation), and the cells were cultured for another 2 days. The resulting population of the non-adherent cells was used as the dendritic cells.

The thus prepared dendritic cells were suspended in AIM-V medium at a cell density of $1 \times 10^6$ cells/mL. Each of the peptides which were selected in the above described (1) and expected to be capable of binding to the HLA-A0201 molecule was added to the cells at a concentration of 10 μg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000 U/mL) and IL-12 (10 ng/ml, manufactured by Genzyme Corporation), and then placed in wells of a 24-well plate at a population of $1 \times 10^5$ cells per well. Further, the prepared T cell population was added to the wells at a population of $1 \times 10^6$ cells per well, and the cells were cultured under the conditions of 37° C. and 5% $CO_2$. Seven days later, each culture supernatant was discarded. Then, dendritic cells obtained in the same manner as described above by the treatment with each peptide and the subsequent X-ray irradiation were suspended (cell density: $1 \times 10^5$ cells/mL) in AIM-V medium containing 10% human AB serum (manufactured by Nabi Biopharmaceuticals Inc.), IL-7 (10 U/mL, manufactured by Genzyme Corporation) and IL-2 (10 U/mL, manufactured by Genzyme Corporation), and the resulting suspension was added to the wells of the 24-well plate at a population of $1 \times 10^5$ cells per well, followed by further culturing the cells. The same procedures were repeated 4 times at intervals of 7 days, and the stimulated T cells were then collected. Thereafter, the induction of CD8-positive T cells was confirmed by flow cytometry.

Further, the same treatment as described above was carried out, using as a negative control, a peptide (SEQ ID NO: 74) having a sequence outside the scope of the present invention; and using as Comparative Examples, known peptides (SEQ ID NOs: 75 to 83) which bind to the HLA-A0201 molecule, and the PDS5A protein which had been prepared according to Example 5 in WO 2011/027807 and which consists of the amino acid sequence represented by SEQ ID NO: 2.

The induction of peptide epitope-reactive CD8-positive T cells was attempted also for the peptides expected to be capable of binding to the HLA-A24 molecule, in the same manner as described above, using dendritic cells and a T cell population induced from peripheral blood of an HLA-A24-positive healthy individual. Further, the same treatment as described above was carried out, using as a negative control, a peptide (SEQ ID NO: 84) having a sequence outside the scope of the present invention; and using as a Comparative Example, the PDS5A protein consisting of the amino acid sequence represented by SEQ ID NO: 2.

Example 3: Determination of Cytotoxic T Cell Antigen Epitopes (1) IFN-γ-Producing Ability In order to examine the specificity of the respective T cells induced in Example 2 (2), to the respective epitope peptides and the protein, dendritic cells expressing the HLA-A0201 molecule were pulsed with various types of polypeptides. The dendritic cells were prepared by culturing in AIM-V medium supplemented with each polypeptide at a concentration of 10 µg/mL under the conditions of 37° C. and 5% $CO_2$ for 4 hours. As the various types of polypeptides, the respective polypeptides represented by the amino acid sequences of SEQ ID NOs: 3 to 19 and expected to be capable of binding to the HLA-A0201 molecule, the negative control polypeptide (SEQ ID NO: 74), the known polypeptides (SEQ ID NOs: 75 to 83) which bind to the HLA-A0201 molecule, and the PDS5A protein consisting of the amino acid sequence represented by SEQ ID NO: 2, were used. To $5\times10^4$ dendritic cells which had been pulsed with each peptide, $5\times10^3$ T cells were added, and the cells were cultured for 24 hours in AIM-V medium containing 10% human AB serum, in a 96-well plate. Each supernatant after the cultivation was collected, and the amount of IFN-γ produced was measured by ELISA.

Figure 2:
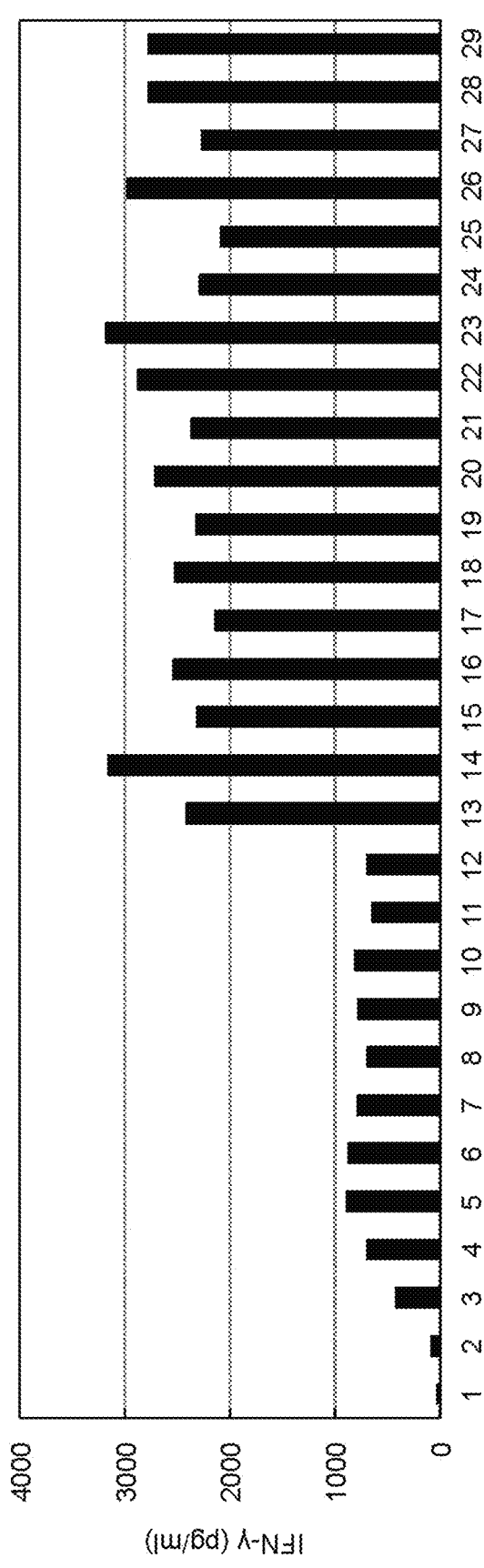
FIG. 2 shows that CD8-positive T cells specific to each of polypeptides consisting of the amino acid sequences represented by SEQ ID NOs: 3 to 19 recognize the complex consisting of the polypeptide and HLA-A0201 and produce IFN-γ.

As a result, a clearly higher IFN-γ production was observed in the supernatants of Lanes 13 to 29 in which the dendritic cells pulsed with the polypeptides having the amino acid sequences represented by SEQ ID NOs: 3 to 19 were used, as compared to the supernatants of Lanes 1 and 2 in which the dendritic cells not pulsed with any polypeptide and the dendritic cells pulsed with the negative control polypeptide, respectively, were used (FIG. 2). These results revealed that the peptides of SEQ ID NOs: 3 to 19 are T cell epitope peptides having an ability to specifically stimulate the proliferation of HLA-A0201-positive CD8-positive T cells, and to induce IFN-γ production. Further, it has also been revealed that the amounts of IFN-γ produced by T cells stimulated with these peptides were markedly higher than the amounts of IFN-γ produced by T cells stimulated with the known peptides which bind to the HLA-A0201 molecule and which have the amino acid sequences represented by SEQ ID NOs: 75 to 83 (Lanes 4 to 12), and with the full-length PDS5A protein consisting of the amino acid sequence represented by SEQ ID NO: 2 (Lane 3). In other words, these results indicate that the polypeptides of SEQ ID NOs: 3 to 19 have a markedly higher immune-inducing activity as compared to that of the peptides previously reported. In addition, although the sequences of SEQ ID NOs: 3 to 19 having the above described immune-inducing activity are included in the amino acid sequence of the full-length PDS5A protein represented by SEQ ID NO: 2, the amount of IFN-γ produced by the T cells stimulated with the full-length PDS5A protein of SEQ ID NO: 2 was low. The reason for this is thought to be that the full-length PDS5A protein failed to demonstrate sufficient immune-inducing activity, because the amino acid sequence of the full-length PDS5A protein also includes a number of sequences which inhibit the immunity-inducing activity.

Further, in order to examine the specificity of each of the peptide epitope-reactive CD8-positive T cells induced in Example 3 (2) using the polypeptides having the amino acid sequences represented by SEQ ID NOs: 20 to 34, to peptide epitopes, the amount of IFN-γ produced by the T cells, against dendritic cells expressing the HLA-A24 molecule, which dendritic cells had been pulsed with each of: the polypeptides of SEQ ID NOs: 20 to 34 (Lanes 4 to 18); the negative control polypeptide having the amino acid sequence represented by SEQ ID NO: 84; and the full-length PDS5A protein having the amino acid sequence represented by SEQ ID NO: 2; was measured by ELISA, in the same manner as described above.

Figure 3:
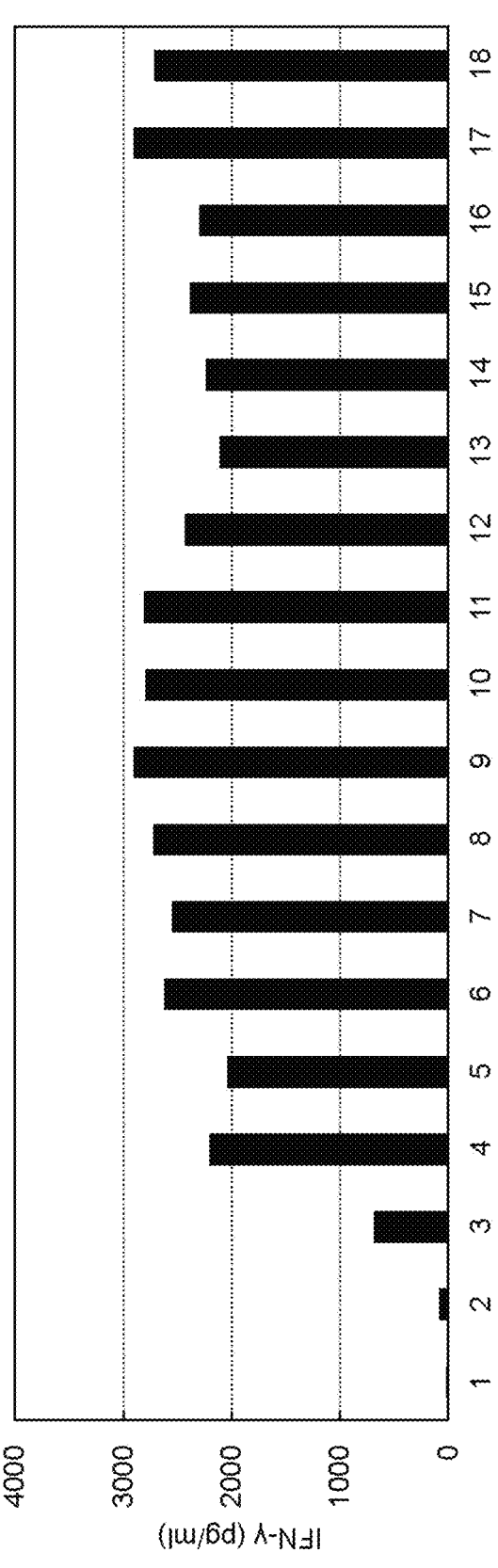
FIG. 3 shows that CD8-positive T cells specific to each of polypeptides consisting of the amino acid sequences represented by SEQ ID NOs: 20 to 34 recognize the complex consisting of the polypeptide and HLA-A24 and produce IFN-γ.

As a result, a markedly higher IFN-γ production was observed in the culture supernatants of Lanes 4 to 18 in which the dendritic cells pulsed with the polypeptides of SEQ ID NOs: 20 to 34 were used, as compared to the supernatants of Lanes 1 and 2 in which the dendritic cells not pulsed with any polypeptide and the dendritic cells pulsed with the negative control polypeptide, respectively, were used (Figure. 3).

These results revealed that the polypeptides of SEQ ID NOs: 20 to 34 are T cell epitope peptides having an ability to specifically stimulate the proliferation of HLA-A24-positive CD8-positive T cells, and to induce IFN-γ production. Further, it has also been revealed that that the amounts of IFN-γ produced by T cells stimulated with these polypeptides were markedly higher than the amounts of IFN-γ produced by T cells stimulated with the full-length PDS5A protein having the amino acid sequence represented by SEQ ID NO: 2. The reason for this is thought to be that the full-length PDS5A protein failed to demonstrate sufficient immunity-inducing activity, due to the same reason as described above.

(2) Cytotoxicity Assay

Subsequently, the following were examined: whether or not the polypeptides having the amino acid sequences represented by SEQ ID NOs: 3 to 19, which are used in the present invention, are presented on the HLA-A0201 molecules on tumor cells which are HLA-A0201-positive and which express human PDS5A protein; whether or not the CD8-positive T cells stimulated with the polypeptides according to the present invention can damage the tumor cells which are HLA-A0201-positive and which express the human PDS5A protein; and further, whether or not the above described CD8-positive T cells have a markedly higher ability to damage the tumor cells as compared to the CD8-positive T cells stimulated with the known peptides (SEQ ID NOs: 75 to 83) and those stimulated with the PDS5A protein.

Each of the total 10 types of cell lines whose expression of human PDS5A protein has been confirmed, namely: a human glioma (malignant brain tumor) cell line U251 cells; a leukemia cell line Jurkat cells; a liver cancer cell line SK-Hep1; a breast cancer cell line MCF7; a pancreatic cancer cell line Panc1; an ovarian cancer cell line OVCAR3; a renal cancer cell line A498; a colorectal cancer cell line HCT116; a stomach cancer cell line KATO3; and a lung cancer cell line NCI-H522 (purchased from ATCC); were collected into a 50 mL centrifugal tube, in an amount of $1\times10^6$ cells each. After adding 100 µCi of chromium 51 thereto, the cells were incubated at 37° C. for 2 hours. Thereafter, each type of the cells were washed 3 times with RPMI medium (manufactured by Gibco Brl Co.) containing 10% fetal bovine serum (hereinafter, referred to as FBS; manufactured by Gibco Brl Co.) and placed in wells of a 96-well V-bottom plate at a population of $1\times10^3$ cells per well. To each well, $5\times10^4$ cells of HLA-A0201-positive CD8-positive T cells suspended in RPMI medium containing 10% FBS, which cells had been induced by stimulation with each of: the polypeptides having the amino acid sequences represented by SEQ ID NOs: 3 to 19, the negative control polypeptides (SEQ ID NO: 74), the known peptides (SEQ ID NOs: 75 to 83) and the full-length PDS5A protein having the amino acid sequence represented by SEQ ID NO: 2; were further added, followed by culturing for 4 hours under the conditions of 37° C. and 5% $CO_2$. After the cultivation, the amount of chromium 51 released from the damaged tumor cells into each culture supernatant was measured, whereby the cytotoxic activity of the CD8-positive T cells induced by stimulation with each of the polypeptides and the protein was calculated.

Figure 4A:
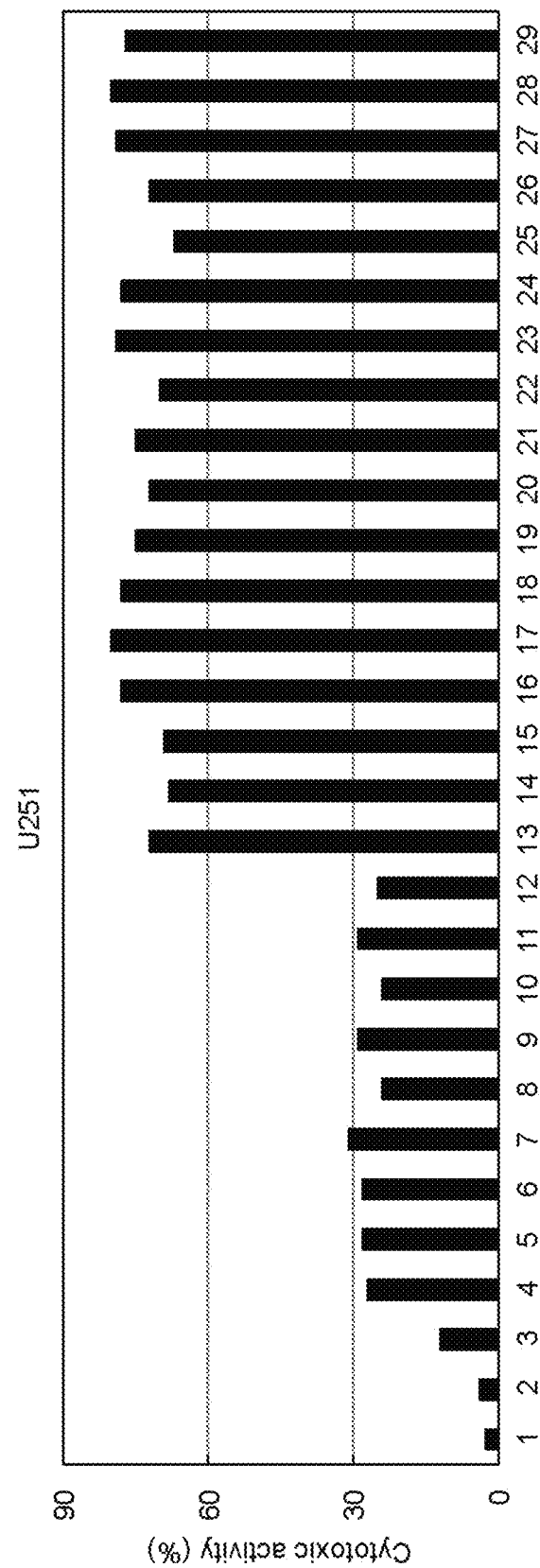
FIG. 4A Figure. 4A shows the cytotoxic activity, against cancer cells, of CD8-positive T cells specific to each of the polypeptides consisting of the amino acid sequences represented by SEQ ID NOs: 3 to 19.
Figure 4B:
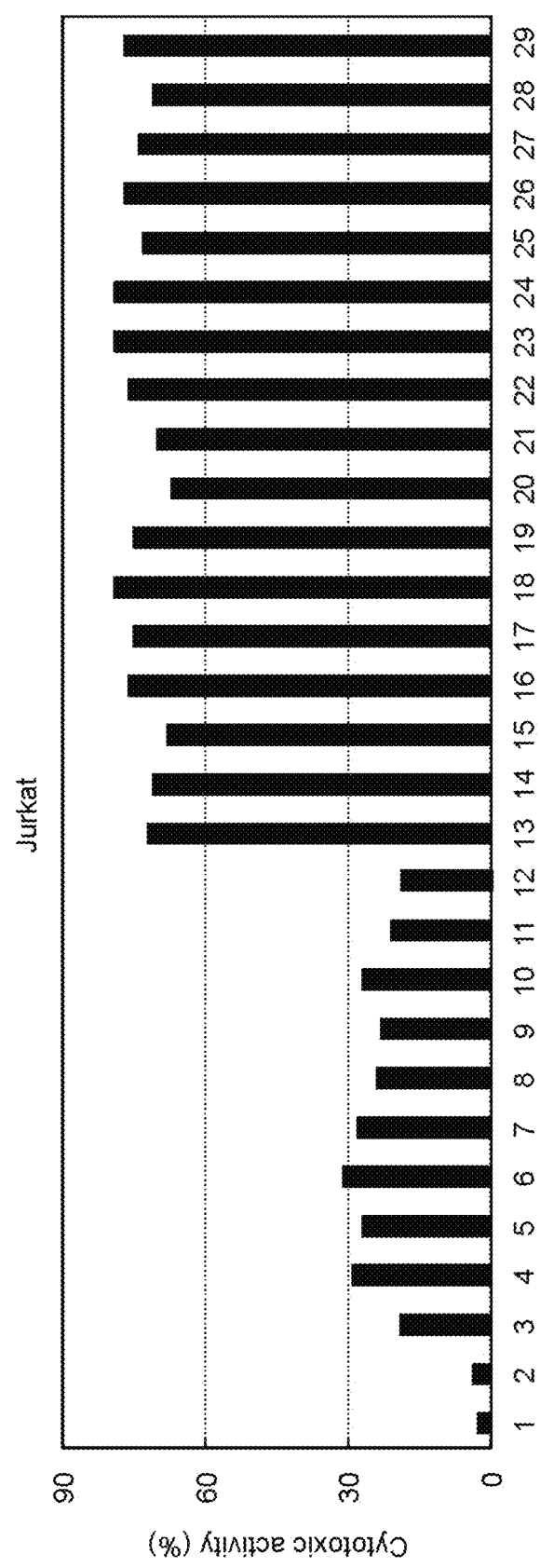
FIG. 4B shows the cytotoxic activity, against cancer cells, of CD8-positive T cells specific to each of the polypeptides consisting of the amino acid sequences represented by SEQ ID NOs: 3 to 19.

As a result, it has been revealed that the HLA-A0201-positive CD8-positive T cells induced by stimulation with the polypeptides having the amino acid sequences represented by SEQ ID NOs: 3 to 19 exhibit a markedly high cytotoxic activity, which is well above the generally predictable range, against all of the above described 10 types of cells. As representative examples, the cytotoxic activity against the U251 cells and the Jurkat cells are shown in FIG. 4A and FIG. 4B, respectively. It can be seen that the CD8-positive T cells stimulated by the polypeptides having the amino acid sequences represented by SEQ ID NOs: 3 to 19 (Lanes 13 to 29, respectively) exhibit a markedly higher cytotoxic activity against the U251 cells and the Jurkat cells, as compared to the CD8-positive T cells stimulated by the polypeptides having the amino acid sequences represented by SEQ ID NOs: 75 to 83 (Lanes 4 to 12, respectively), and those stimulated by the full-length PDS5A protein (Lane 3). On the other hand, the CD8-positive T cells induced with the negative control polypeptide (Lane 2) did not show any cytotoxic activity, the result being roughly the same as the case of Mock (Lane 1). These results suggest that each of the polypeptides of SEQ ID NOs: 3 to 19 used in the present invention is presented on the HLA-A0201 molecules on tumor cells which are HLA-A0201-positive and which express human PDS5A polypeptide, and in addition, that the polypeptides according to the present invention have an ability to induce CD8-positive cytotoxic T cells capable of damaging such tumor cells, to a level well above a predictable range. Further, regardless of the fact that the amino acid sequence of the full-length PDS5A protein includes the sequences of SEQ ID NOs: 3 to 19, the CD8-positive T cells stimulated with the full-length PDS5A protein exhibited a markedly lower cytotoxic activity, as compared to that of the CD8-positive T cells stimulated with the polypeptides having the amino acid sequences of SEQ ID NOs: 3 to 19 (Lanes 3, 13 to 29). The reason for this is thought to be that the PDS5A protein failed to induce T cells having a high cytotoxic activity, because the amino acid sequence of the PDS5A protein includes a number of sequences which inhibit the immunity-inducing activity.

Similarly, it was examined whether or not the polypeptides of SEQ ID NOs: 20 to 34 are presented on the HLA-A24 molecules on tumor cells which are HLA-A24-positive and which express human PDS5A protein; whether or not the CD8-positive T cells stimulated with the polypeptides according to the present invention can damage the tumor cells which are HLA-A24-positive and which express the human PDS5A protein; and further, whether or not the above described CD8-positive T cells have a markedly higher ability to damage the tumor cells as compared to the CD8-positive T cells stimulated with the PDS5A protein.

Chromium 51 was allowed to be incorporated into the total 6 types of cell lines which are HLA-A24-positive and which express human PDS5A protein, namely: a leukemia cell line THP1; a human glioma cell line KNS-42; a liver cancer cell line SK-Hep1; a renal cancer cell line Caki1; a colorectal cancer cell line SW480; and a stomach cancer cell line KATO3 (purchased from RIKEN and ATCC). Each type of the cells were cultured with the HLA-A24-positive CD8-positive T cells which had been induced by stimulation with each of: the polypeptides having the amino acid sequences represented by SEQ ID NOs: 20 to 34; the negative control polypeptide (SEQ ID NO: 84); and the full-length PDS5A protein, and the amount of chromium 51 released from the damaged cells into each culture supernatant was measured.

Figure 5A:
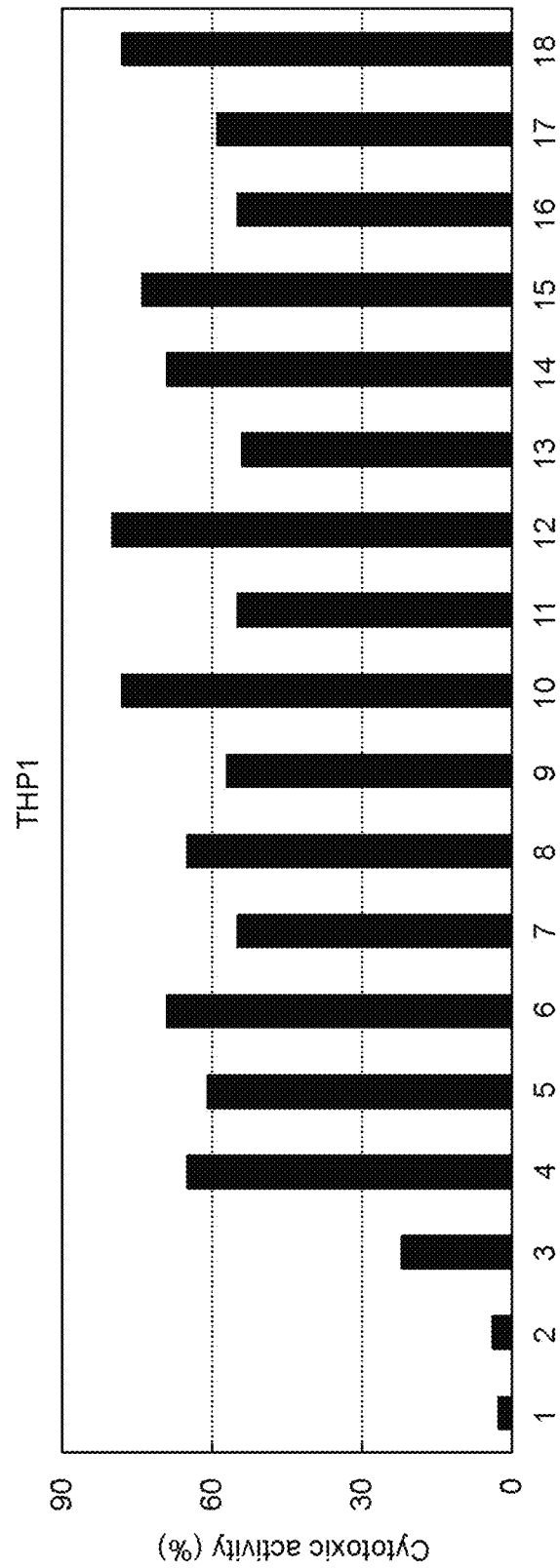
FIG. 5A is a graph showing the cytotoxic activity, against cancer cells, of CD8-positive T cells specific to each of the polypeptides consisting of the amino acid sequences represented by SEQ ID NOs: 20 to 34.
Figure 5B:
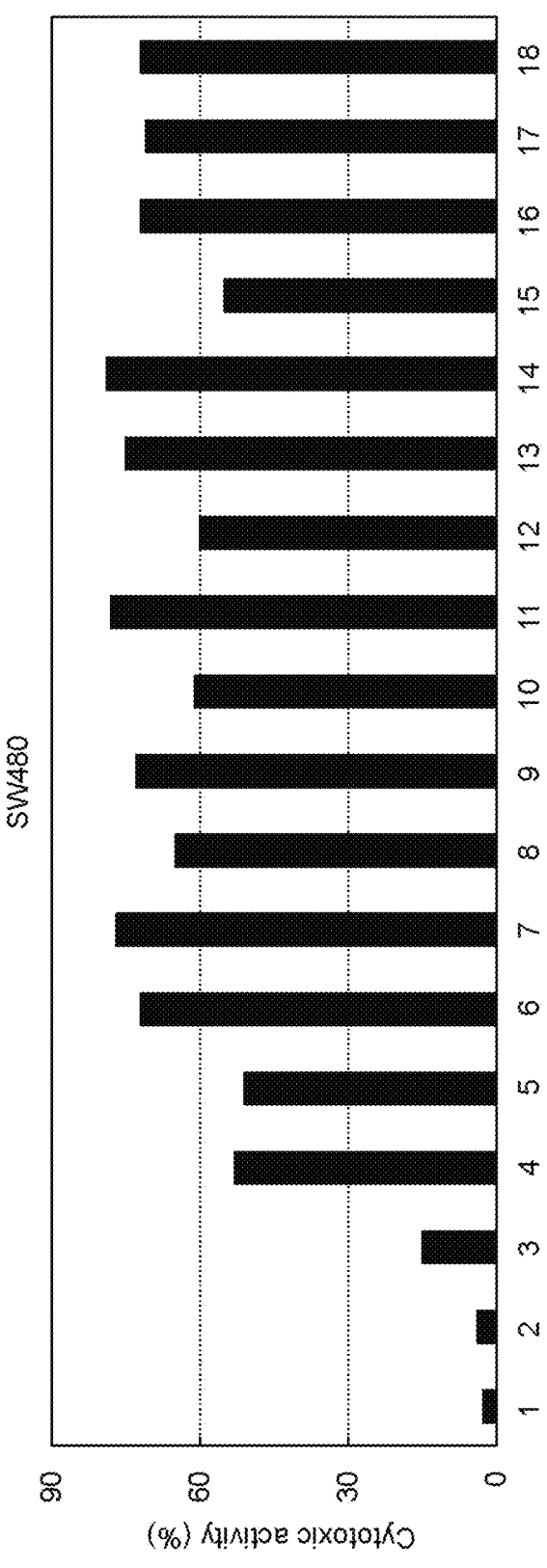
FIG. 5B shows the cytotoxic activity, against cancer cells, of CD8-positive T cells specific to each of the peptides consisting of the amino acid sequences represented by SEQ ID NOs: 20 to 34.

As a result, it has been revealed that the HLA-A24-positive CD8-positive T cells stimulated with the polypeptides having the amino acid sequences represented by SEQ ID NOs: 20 to 34 exhibit a markedly high cytotoxic activity, which is well above the generally predictable range, against all types of cancer cells used. As representative examples, the cytotoxic activity against the THP1 cells and the SW480 cells are shown in FIG. 5A and FIG. 5B, respectively. It can be seen that the CD8-positive T cells stimulated by the polypeptides having the amino acid sequences represented by SEQ ID NOs: 20 to 34 (Lanes 4 to 18, respectively) exhibit a markedly higher cytotoxic activity against the THP1 cells and the SW480 cells, as compared to the CD8-positive T cells (Lane 3) stimulated by the full-length PDS5A protein. On the other hand, the CD8-positive T cells induced with the negative control polypeptide (Lane 2) did not show any cytotoxic activity, the result being roughly the same as the case of Mock (Lane 1). Thus, it can be seen that each of the polypeptides of SEQ ID NOs: 20 to 34 is presented on the HLA-A24 molecules on cells which are HLA-A24-positive and which express human PDS5A protein, and these results suggest that the polypeptides according to the present invention have an ability to induce CD8-positive cytotoxic T cells capable of damaging such cells.

On the other hand, when the above described 14 types of cancer cells were exposed to the polypeptides represented by the amino acid sequences of SEQ ID NOs: 3 to 34 and the full-length PDS5A protein consisting of the amino acid sequence represented by SEQ ID NO: 2, no cancer cells were killed at all. This confirmed the fact that these polypeptides do not have an activity to directly kill the cancer cells.

The cytotoxic activity was determined as described above, by mixing $5\times10^4$ cells of the CD8-positive T cells stimulated and induced with each of the polypeptides used in the present invention and $1\times10^3$ cells of each type of the tumor cells into which chromium 51 was incorporated; culturing each mixture of cells for 4 hours; measuring the amount of chromium 51 released into each culture medium after the cultivation; and calculating the cytotoxic activity of the CD8-positive T cells against each type of the tumor cells (referred to as target cells) according to the following formula*.

cytotoxic activity (%)=amount of chromium 51 released from target cells upon addition of CD8-positive T cells/amount of chromium 51 released from target cells upon addition of 1 N hydrochloric acid×100                    *Formula:

Example 4: Induction of CD4-Positive T Cells
Reactive with Peptide Epitopes Derived from
PDS5A Protein-Derived Peptide For predicting CD4-positive T cell antigen epitopes, the amino acid sequence of the human PDS5A protein was analyzed with a computer-based prediction program using the SYFPEITHI algorithm (by Rammensee), and 33 types of peptides represented by SEQ ID NOs: 35 to 67 and expected to be HLA class II-binding peptides were selected. All the selected peptides were synthesized by Greiner Japan Co. Ltd. that provides custom peptide synthesis services.

Peripheral blood was separated from the blood of an HLA-DRB1*04-positive healthy individual. The peripheral blood was layered on Lymphocyte separation medium (manufactured by Organon Teknika Corporation), and centrifuged at 1,500 rpm at room temperature for 20 minutes. A PBMC-containing fraction was collected and washed 3 times (or more) with a cold phosphate buffer solution to obtain PBMCs. The thus obtained PBMCs were suspended in 20 mL of AIM-V medium (manufactured by Life Technologies, Inc.), and allowed to adhere to a culture flask (manufactured by Falcon Plastics Co.) for 2 hours under the conditions of 37° C. and 5% $CO_2$. Non-adherent cells were used for the preparation of T cells, and adherent cells were used for preparing dendritic cells.

The adherent cells were cultured in AIM-V medium in the presence of IL-4 (1,000 U/ml) and GM-CSF (1,000 U/ml). Six days later, the medium was replaced with AIM-V medium supplemented with IL-4 (1,000 U/mL), GM-CSF (1,000 U/mL), IL-6 (1,000 U/mL, manufactured by Genzyme Corporation), IL-1B (10 ng/ml, manufactured by Genzyme Corporation) and TNF-α (10 ng/mL, manufactured by Genzyme Corporation), and the cells were cultured for another 2 days. The obtained population of the non-adherent cells was used as the dendritic cells.

The thus prepared dendritic cells were suspended in AIM-V medium at a cell density of $1 \times 10^6$ cells/mL. Each of the polypeptides of SEQ ID NOs: 35 to 67, the negative control polypeptide (SEQ ID NO: 85) and the PDS5A protein consisting of the amino acid sequence represented by SEQ ID NO: 2 was added to the cells at a concentration of 10 mg/mL, followed by culturing for 4 hours under the conditions of 37° C. and 5% $CO_2$, using a 96-well plate. After the cultivation, the cells were irradiated with X-ray (3000 rad), washed with AIM-V medium, suspended in AIM-V medium containing 10% human AB serum (manufactured by Nabi Biopharmaceuticals Inc.), IL-6 (1,000 U/mL) and IL-12 (10 ng/ml, manufactured by Genzyme Corporation), and then placed in wells of a 24-well plate at a population of $1 \times 10^5$ cells per well. Further, the prepared T cell population was added to the wells at a population of $1 \times 10^6$ cells per well, and the cells were cultured under the conditions of 37° C. and 5% $CO_2$. Seven days later, each culture supernatant was discarded. Then, dendritic cells treated with each peptide obtained in the same manner as described above or the PDS5A protein followed by X-ray irradiation were suspended in AIM-V medium containing 10% human AB serum (manufactured by Nabi Biopharmaceuticals Inc.) and IL-2 (10 U/mL, manufactured by Genzyme Corporation), and the resulting suspension was added to the wells of the 24-well plate at a population of $1 \times 10^5$ cells per well, followed by further culturing the cells. The same procedures were repeated 4 times at intervals of 7 days, and the stimulated T cells were then collected. Thereafter, the induction of CD4-positive T cells was confirmed by flow cytometry. As a result, the induced T cells in each well were confirmed to be proliferated.

Example 5: Determination of PDS5A
Protein-Derived Helper T Cell Antigen Epitopes
which Stimulate HLA-DRB1*04-Positive
CD4-Positive T Cells In order to examine the specificity of the respective CD4-positive T cells induced in the above described Example 4 to the respective peptide proteins, the PBMCs expressing HLA-DRB1*04 molecules were pulsed with various types of polypeptides. The PBMCs were prepared by culturing in AIM-V medium supplemented with each polypeptide at a concentration of 10 μg/mL under the conditions of 37° C. and 5% $CO_2$ for 4 hours. As the various types of polypeptides, the respective polypeptides represented by the amino acid sequences of SEQ ID NOs: 35 to 67, the negative control polypeptide (SEQ ID NO: 85) and the full-length PDS5A protein consisting of the amino acid sequence represented by SEQ ID NO: 2 were used. To $5 \times 10^4$ PBMCs which had been pulsed with each peptide, $5 \times 10^4$ CD4-positive T cells were added, and the cells were cultured for 24 hours in AIM-V medium containing 10% human AB serum, in a 96-well plate. Each supernatant after the cultivation was collected, and the amount of produced IFN-γ was measured by ELISA.

As a result, an IFN-γ production of 1,000 μg/mL or more was confirmed in the culture supernatants in the wells of PBMCs pulsed with the respective peptides of SEQ ID NOs: 35 to 67. On the other hand, the production of IFN-γ was barely observed in the culture supernatants in the well of PBMCs pulsed with the negative control polypeptide and in the well of the dendritic cells alone not pulsed with any polypeptide. Thus, it has been revealed that the polypeptides represented by the amino acid sequences SEQ ID NOs: 35 to 67 are T cell epitope peptides having an ability to specifically stimulate and propagate the HLA-DRB1*04-positive CD4-positive T cells, and to induce the production of IFN-γ. Further, regardless of the fact that the amino acid sequence of the full-length PDS5A protein includes the above described sequences of SEQ ID NOs: 35 to 67 having an immunity-inducing activity, the amount of IFN-γ produced in the culture supernatant in the well of PBMC cells pulsed with the full-length PDS5A protein was extremely low. The reason for this is thought to be that the PDS5A protein failed to demonstrate sufficient immunity-inducing activity, because the amino acid sequence of the PDS5A protein includes a number of sequences which inhibit the immunity-inducing activity.

Subsequently, it was examined whether or not the polypeptides of SEQ ID NOs: 35 to 67 having an ability to stimulate the proliferation of the HLA-DRB1*04-positive T cells are epitopes which are naturally processed from the PDS5A protein within the antigen-presenting cells and presented on HLA-DR. A lysate of HEK293 cells (purchased from ATCC) transiently expressing the PDS5A protein was added to immature dendritic cells to allow the digestion of the protein, and the maturation of the dendritic cells. Then, it was examined whether or not the T cells stimulated with each of the polypeptides of SEQ ID NOs: 35 to 67, the negative control polypeptide and the PDS5A protein are stimulated by the resulting dendritic cells. Peripheral blood was separated from the blood of an HLA-DRB1*04-positive healthy individual. The peripheral blood was layered on Lymphocyte separation medium, and centrifuged at 1,500 rpm at room temperature for 20 minutes. The interphase containing PBMCs was collected and washed 3 times (or more) with a cold phosphate buffer solution to obtain PBMCs. The thus obtained PBMCs were suspended in 20 mL of AIM-V medium, and allowed to adhere to a culture flask (manufactured by Falcon Plastics Co.) for 2 hours under the conditions of 37° C. and 5% $CO_2$. The adherent cells were cultured in AIM-V medium in the presence of IL-4 (1,000 U/mL) and GM-CSF (1,000 U/mL) for 6 days, to obtain immature dendritic cells. The above described lysate was added to $5\times10^5$ immature dendritic cells, followed by culturing in AIM-V medium supplemented with IL-4 (1,000 U/mL), GM-CSF (1,000 U/mL), IL-6 (1,000 U/mL), IL-1β (10 ng/ml) and TNF-α (10 ng/mL) for 2 days. The cultured dendritic cells were irradiated with X-ray (3000 rad), washed with AIM-V medium, suspended in AIM-V medium containing 10% human AB serum, and then placed in wells of a 96-well plate at a population of $3.3\times10^4$ cells per well. To each well, $5\times10^4$ T cells stimulated with each of the polypeptides of SEQ ID NOs: 35 to 67, the negative control polypeptide and the PDS5A protein were added, and the cells were cultured under the conditions of 37° C. and 5% $CO_2$ for 24 hours. Each supernatant after the cultivation was collected, and the amount of produced IFN-γ was measured by ELISA.

Figure 6:
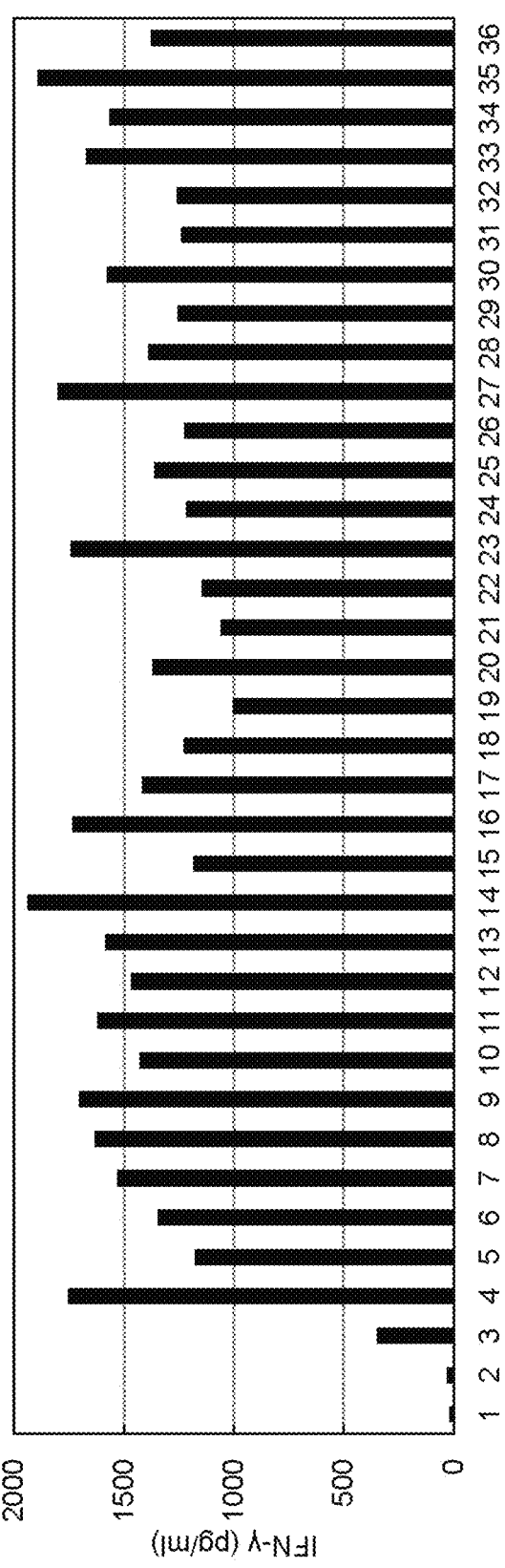
FIG. 6 is a graph showing that CD4-positive T cells specific to each of the polypeptides consisting of the amino acid sequences represented by SEQ ID NOs: 35 to 67 recognize the complex of the polypeptide and HLA-DRB1*04 and produce IFN-γ.

As a result, as shown in FIG. 6, it has been found out that the T cells of Lanes 4 to 36 which were stimulated with the polypeptides of SEQ ID NOs: 35 to 67, respectively, produced IFN-γ in response to stimulation by the dendritic cells to which the PDS5A protein was added. On the other hand, the production of IFN-γ was barely observed in the T cells of Lane 2 stimulated with the negative control polypeptide and the T cells of Lane 1 not stimulated with any polypeptide. Thus, it has been revealed that the polypeptides of SEQ ID NOs: 35 to 67 are epitopes which are naturally processed from the PDS5A protein within the antigen-presenting cells and presented on HLA-DR. Further, the production of IFN-γ in the T cells of Lane 3 pulsed with the full-length PDS5A protein was extremely low, also in the present experiment. The reason for this is thought to be that the full-length PDS5A protein failed to demonstrate sufficient immunity-inducing activity, because the amino acid sequence of the full-length PDS5A protein includes a number of sequences which inhibit the immunity-inducing activity.

INDUSTRIAL APPLICABILITY

The immune inducer according to the present invention containing a polypeptide which exhibits an anti-tumor activity against various types of cancers is useful in the treatment or prevention of cancer, or in the detection of cancer.

All publications, patents, and patent applications cited in this specification are incorporated herein by reference in their entirety.

---

SEQUENCE LISTING

```
Sequence total quantity: 86
SEQ ID NO: 1             moltype = DNA  length = 7190
FEATURE                  Location/Qualifiers
source                   1..7190
                         mol_type = genomic DNA
                         organism = Homo sapiens
CDS                      541..4554
SEQUENCE: 1
ggccggcgga ggaaggggag ggagcgagga gcgcgcgctg ctctcgcgtg ctctcgcgcc   60
gctcgcgtga ccggccggtg tgtgcgcgag gccccggctc ccggggcacg gacggccggg  120
cgcgcgcctc tgcgaggggc gtccgggtcc gagtcggcgg tccgggccgg cgcgaggtgc  180
gtgcgggcgg gccgcggggg tcccggacgg acacaagcgc acacactccc ggaggagcct  240
tcgaggctgc tcttcctcgg ccagacggag agcggcactg tctccccgcc cagcgctcac  300
tcgccccgcg tctcccccg cggcggctgc tcctcctcgg caccgccagc cccagccgcg  360
ctcccgggcg ggcgggcggc ggcggcgcg gcggcgggac ccgcggagcc gctttgtgtg  420
cagcccgact aggggcggcg gcgcaaccac ctgacagagg cccgggcgct cgatgcacct  480
tccgcccgca tgaggaggag aggccggtag aggactgtga accaaaagtt gtcccccagg  540
atggacttca ccgcgcagcc caagcctgcc actgccctct gtggcgtcgt gagtgccgac  600
gggaagatcg cttaccctcc gggggtaaaa gagatcaccg acaagatcac cacggacgag  660
atgatcaaac gcctgaagat ggtagtgaaa acctttatgg atatggatca ggactcagaa  720
gatgaaaaac agcagtatct cccactagcc ttgcatcttg catctgaatt cttcctcagg  780
aacccaata aagatgtgcg tctccttgta gcatgttgtt tggctgatat ctttcgtatc  840
tatgccccag aagctccata tacttcccat gataaactta aggacatatt tttgtttatt  900
accagacaat taaaaggttt ggaggataca aagagtccac agtttaatag atacttttat  960
ttattagaga atttagcttg ggttaaatca tataacatct gctttgaatt ggaagattgc 1020
aatgaaattt ttattcagct ttttagaact ctcttctcag tgatcaacaa tagccacaat 1080
aagaaggtac aaatgcacat gctagatttg atgagttcta tcatcatgga aggtgatgga 1140
gttactcaag aattattgga ctccattctt attaacctca ttcctgcaca taagaactta 1200
aataaacagt cctttgacct tgcaaaagtg ctattgaaaa gaacagtcca gactattgag 1260
gcatgcattg ctaatttttt caatcaagtc ctggtgctgg gaagatcatc agtaagtgat 1320
ttgtcagaac atgtatttga tctgattcag gaactttttg ctatagatcc tcatttatta 1380
ttatccgtca tgccacagct tgaattcaaa ctaaagagca atgatggaga agagcgatta 1440
gctgttgttc gacttctagc taaattgttt ggctccaaag attctgattt ggcaacacag 1500
aatcgtcctc tttggcaatg ttttcttgga cgatttaatg atattcatgt tcctgtgaga 1560
ttagaaagtg tgaaatttgc cagtcattgt ttaatgaatc acccagattt agcgaaggat 1620
ctcacagaat atttaaaggt tagatcacat gatccagaag aagctattcg tcatgatgtc 1680
attgttacta taataacagc tgccaagagg gacctggcct tagtaaatga tcagctgctt 1740
ggctttgtaa gggaaagaac actggataaa cggtggcgag taagaaaaga agctatgatg 1800
ggtctggctc agctttataa gaaatactgt cttcatggtg aagcaggaaa ggaagctgca 1860
gagaaagtca gctggataaa ggacaaactt ctgcatattt attatcagaa cagcattgac 1920
gacaaactgt tggtagagaa aatctttgct cagtatcttg tcccccacaa cctgaaaca 1980
gaagagagaa tgaaatgctt atattactta tatgctagtt tggatccaaa tgctgtaaaa 2040
gctctcaacg aaatgtggaa gtgtcagaac atgcttcgga gccatgtacg cgaactattg 2100
gatttgcaca agcagcctac atcagaggct aactgttctg ccatgtttgg aaaactgatg 2160
```

-continued

```
accatagcaa agaatttgcc tgaccccggg aaagcacaag attttgtgaa gaaatttaac  2220
caggttctcg gcgatgatga gaaacttcgg tctcagttgg agttattaat tagcccaacc  2280
tgttcttgca aacaagcaga tatttgtgtg agagaaatag cccggaaact tgcaaatcct  2340
aagcaaccaa caaatccttt tctagagatg gtcaaatttc tgttggaaag aatcgcacct  2400
gtgcacattg attcagaagc cataagtgca ctagtgaaat tgatgaataa gtcaatagag  2460
gggacagcag atgatgaaga ggagggtgta agtccagata cagctatccg ttcaggactt  2520
gaacttctta aggttctgtc ttttacacat cctacctcgt tccactctgc agagacatat  2580
gagtccttgt tacagtgcct aagaatggag gatgacaagg tagcagaagc tgctattcaa  2640
atttttagaa atacaggtca caaaatagaa acagacccttc cccagatacg atcgacctta  2700
attcccattt tacatcaaaa agcaaagagg ggtactccac accaagcaaa acaggctgtg  2760
cactgtatac acgccatatt cacaaataaa gaagtccagc ttgcacagat ttttgagcca  2820
ctcagtagga gtctgaatgc tgatgtgcca gaacaactta taactccatt agtttcattg  2880
ggccacattt ctatgttagc accagatcag tttgcttccc caatgaaatc tgtagtagca  2940
aattttattg tgaaagatct gctaatgaat gacaggtcaa caggtgaaaa gaatggaaaa  3000
ctgtggtctc cagatgaaga ggtttcccct gaagtactag caaaggtaca ggcaattaaa  3060
cttctggtaa ggtggctgtt gggtatgaaa aacaaccagt ctaaatctgc caattcaacc  3120
cttcggttat tatcagcgat gttggttagt gagggtgacc tgacagagca aaagaggatc  3180
agtaaatctg atatgtctcg cttgcgatta gctgctggta gtgccataat gaagcttgct  3240
caggaacctt gttaccatga aattattacc ccagaacagt ttcagctctg tgcacttgtt  3300
attaatgatg agtgttacca agtaaggcag atatttgctc agaagctgca taaggcactt  3360
gtgaagttac tgctcccatt ggagtatatg gcgatctttg ccttgtgtgc caaagatcct  3420
gtgaaggaga gaagagcaca cgcacgacaa tgtttactga aaaatatcag tatacgcagg  3480
gaatacatta agcagaatcc tatggctact gagaaaattat tatcactgtt gcctgaatat  3540
gtagttccat acatgattca cctgctagcc catgatccag attttacaag atcacaagat  3600
gttgatcagc ttcgtgatat caaagagtgc ctatggttca tgcttgaagt tttaatgaca  3660
aagaatgaaa acaatagcca tgcctttatg aagaagatgg cagagaacat caagttaacc  3720
agagatgccc agtctccaga tgaatccaag acaaatgaaa aactgtatac agtatgtgat  3780
gtggctctct gtgttataaa tagtaaaagt gctttgtgca atgcagattc accaaaggac  3840
ccagtcctcc caatgaaatt ttttacacaa cctgaaaagg acttctgtaa cgataagagt  3900
tatatttcag aagagacaag agtacttctg ttaacagcaa agccaaagcc tgctggagta  3960
ctaggtgcag taaataagcc tttatcagca acgggaagga aaccctatgt tagaagcact  4020
ggcactgaga ctggaagcaa tattaatgta aattcagagc tgaacccttc aaccggaaat  4080
cgatcaaggg aacagagttc agaggcagca gaaactggag ttagtgaaaa tgaagagaac  4140
cctgtgagga ttatttcagt cacacctgta aagaatattg acccagtaaa gaataaggaa  4200
attaattctg atcaggctac ccagggcaac atcagcagtg accgaggaaa gaaaagaaca  4260
gtaacagcag ctggtgcaga gaatatccaa caaaaaacag atgagaaagt agatgaatcg  4320
ggacctcccg ccccttccaa acccaggaga ggacgtcgac ccaagtctga atctcagggc  4380
aatgctacca aaaatgatga tctaaataaa cctattaaca agggaaggaa gagagctgca  4440
gtgggtcagg agagccctgg gggtttggaa gcaggtaatg ccaaagcacc caaactgcaa  4500
gatttagcca aaaaggcagc accagcagaa agacaaattg acttacaaag gtaaaaatgc  4560
atttgcaaag ggagaaaatg aaggccaaac agaagcaggc tccagcttct gcaaaaactt  4620
ggattcacaa atgtccctga acagaaaatg aagctcactt cagaacacac actctctgcc  4680
ttgaaaacta aagagactat tacttccttt tcacatgacc acaagtcctc tgatggaaat  4740
gtacagcaga aactcttgag agagaggcta aaagcaactc tgttctcccc cttcccctag  4800
actttttctta cgaaaagtca ataattaagc aaattgctta acacttggtt ccagttcctg  4860
cctatctgga gtttaaatgc gtaatacacc attaatttcc acgctgcagt ttttattta  4920
aagaaagtaa caagatgtct ttacactgac actgaaaatt catccatttt agagccagga  4980
attcccatgt tacacaggaa aaaatagaag tctactgaat taattttta aaagaaaaga  5040
gatcagatta aatatttctt tgttttcct tttggaaact tttatgtata attctttctg  5100
cctgcctact tttctgcaaa aatgagatgt acagatttcg gttccctgct atgaaaagtg  5160
atgtggtagc aatttttataa gatgttgcttt ctgattttta tcagagtgag aaaattaaaa  5220
ttattgattt gcaagtagta aacagttcat attttgattt cccctcattt tagtttaata  5280
taatttgcaa taaaatgtaca tattgttgtt tgtttcataa agcatatcac tttaaaatgg  5340
tttttactcc tgtgattatg ttggaatatt tggaatttta aaggagtaaa gactgtccag  5400
catttggttt tataatgttt gtcaccagat ttttattaat gtaaaaaaaa tcaatttta  5460
aaaaatagtt ggactttggc agcttttaag gaaagttgga ggtgttttag gattgctatc  5520
aattttcagc attgtgctat ttggaaataa gtgtgtttgct tttgtctgat ggtctgggct  5580
catttttatg tttattttag aaaactgttg catcaatata ttatgtttct tggcattgtt  5640
cagcataggt aatgtgtgca ctttatgtgt acacataatc atatttaagt tttttgcata  5700
aaataaatgc ttctagatgt catggcagtc tttttaatct ttttatcata tgctttcttg  5760
tgaattttt catgttaaag agctaaagtc ataacatgat tacagtcaac tctccattat  5820
ctatataaaa tagtgactaa gcctcaggtt tttaattttg tgataacaaa ataacgaagg  5880
catgtaagac ctgattctgg aggaacatga aatttgtctt ttctcatgtc cagagttcta  5940
tcctgccccc actgtccact gtagggtcat ccgcaaagcc ctagcagaat gtgctcactc  6000
catttcctta cacgtttcta gcatgggtca gaggaaacaa catttgtgtt ataacttcgt  6060
cttgataggc tgtagtgtac atgggatgta aaacaaacaa gtgtatcaaa ggtggatgat  6120
tctgttagag tgaagtttga gagtaaatgt cacttacgtt tctcatagat aatcaagagt  6180
tggctgtgta ttgactgaaa gatgggtaat tattttaaat atgcatttac acacatttag  6240
gtatcagaag atgcttaggg aacaatggat accaatgata gaaaatgata cctttacagg  6300
ggcagaaaaa tccccactct tccttattgc ctccttcagaa ccccttagaa agtataaaat  6360
attgcctcca acatgctgaa aaagagtatc tatgcataag tatcagagaa gtccctcaag  6420
caatcagtag gtgtgttcta tttagagaga gtttaaagtt ctcttagcat cagacaactt  6480
gattcctaag gtttccagtg tgtcaccaac aaaaagtgca ttgataggga cctttgtctc  6540
ttcctcccctt tgattaattg cccggcatca cagtttacta gattaccaag tgttacatca  6600
tattaaataa aatgtagcag aaccatctgc atcaatatat tcctgtttag atttttgcag  6660
gagagaagtt aaaaggattt gctccttgta tgatgtaagt ggcccacccc aattttgtaa  6720
catgatgcaa gtgtctggca ctaagggaag caagagtagg gttgtggaaa gaccaagctg  6780
atggggaggg acttgtttac gggaattttt ttagtttttcc ttttcaaagg aaaacattaa  6840
aatcccttag gaatttggta ttcacatctc agagaactac aacacaaaag tgcagactta  6900
```

```
tatttgagaa ttaatgttaa cccttttgtgt ctagttttgaa gcttcttgta tttgtctaaa  6960
acaacaagcc agaattttgt atctcctttg ataaaaagtg tgtataatgt aaagtagttt  7020
tgcatattct tgtgctgcac atgggctgaa tttttaaatt tttttaaaa acttgaagca  7080
gaaccttgta atttgtgtaa atgacaagtg taaaatccta ccataaaatg ctaaaaatat  7140
gcactgtttc aaataaaacc aagaaatgca gcattaaaaa aaaaaaaaaa  7190
```

```
SEQ ID NO: 2              moltype = AA   length = 1337
FEATURE                   Location/Qualifiers
source                    1..1337
                          mol_type = protein
                          organism = Homo sapiens
SEQUENCE: 2
MDFTAQPKPA TALCGVVSAD GKIAYPPGVK EITDKITTDE MIKRLKMVVK TFMDMDQDSE  60
DEKQQYLPLA LHLASEFFLR NPNKDVRLLV ACCLADIFRI YAPEAPYTSH DKLKDIFLFI  120
TRQLKGLEDT KSPQFNRYFY LLENLAWVKS YNICFELEDC NEIFIQLFRT LFSVINNSHN  180
KKVQMHMLDL MSSIIMEGDG VTQELLDSIL INLIPAHKNL NKQSFDLAKV LLKRTVQTIE  240
ACIANFFNQV LVLGRSSVSD LSEHVFDLIQ ELFAIDPHLL LSVMPQLEFK LKSNDGEERL  300
AVVRLLAKLF GSKDSDLATQ NRPLWQCFLG RFNDIHVPVR LESVKFASHC LMNHPDLAKD  360
LTEYLKVRSH DPEEAIRHDV IVTIITAAKR DLALVNDQLL GFVRERTLDK RWRVRKEAMM  420
GLAQLYKKYC LHGEAGKEAA EKVSWIKDKL LHIYYQNSID DKLLVEKIFA QYLVPHNLET  480
EERMKCLYYL YASLDPNAVK ALNEMWKCQN MLRSHVRELL DLHKQPTSEA NCSAMFGKLM  540
TIAKNLPDPG KAQDFVKKFN QVLGDDEKLR SQLELLISPT CSCKQADICV REIARKLANP  600
KQPTNPFLEM VKFLLERIAP VHIDSEAISA LVKLMNKSIE GTADDEEEGV SPDTAIRSGL  660
ELLKVLSFTH PTSFHSAETY ESLLQCLRME DDKVAEAAIQ IFRNTGHKIE TDLPQIRSTL  720
IPILHQKAKR GTPHQAKQAV HCIHAIFTNK EVQLAQIFEP LSRSLNADVP EQLITPLVSL  780
GHISMLAPDQ FASPMKSVVA NFIVKDLLMN DRSTGEKNGK LWSPDEEVSP EVLAKVQAIK  840
LLVRWLLGMK NNQSKSANST LRLLSAMLVS EGDLTEQKRI SKSDMSRLRL AAGSAIMKLA  900
QEPCYHEIIT PEQFQLCALV INDECYQVRQ IFAQKLHKAL VKLLLPLEYM AIFALCAKDP  960
VKERRAHARQ CLLKNISIRR EYIKQNPMAT EKLLSLLPEY VVPYMIHLLA HDPDFTRSQD  1020
VDQLRDIKEC LWFMLEVLMT KNENNSHAFM KKMAENIKLT RDAQSPDESK TNEKLYTVCD  1080
VALCVINSKS ALCNADSPKD PVLPMKFFTQ PEKDFCNDKS YISEETRVLL LTGKPKPAGV  1140
LGAVNKPLSA TGRKPYVRST GTETGSNINV NSELNPSTGN RSREQSSEAA ETGVSENEEN  1200
PVRIISVTPV KNIDPVKNKE INSDQATQGN ISSDRGKKRT VTAAGAENIQ QKTDEKVDES  1260
GPPAPSKPRR GRRPKSESQG NATKNDDLNK PINKGRKRAA VGQESPGGLE AGNAKAPKLQ  1320
DLAKKAAPAE RQIDLQR  1337
```

```
SEQ ID NO: 3              moltype = AA   length = 9
FEATURE                   Location/Qualifiers
source                    1..9
                          mol_type = protein
                          organism = Homo sapiens
SEQUENCE: 3
YLPLALHLA  9
```

```
SEQ ID NO: 4              moltype = AA   length = 10
FEATURE                   Location/Qualifiers
source                    1..10
                          mol_type = protein
                          organism = Homo sapiens
SEQUENCE: 4
LLVACCLADI  10
```

```
SEQ ID NO: 5              moltype = AA   length = 9
FEATURE                   Location/Qualifiers
source                    1..9
                          mol_type = protein
                          organism = Homo sapiens
SEQUENCE: 5
YLLENLAWV  9
```

```
SEQ ID NO: 6              moltype = AA   length = 9
FEATURE                   Location/Qualifiers
source                    1..9
                          mol_type = protein
                          organism = Homo sapiens
SEQUENCE: 6
QLFRTLFSV  9
```

```
SEQ ID NO: 7              moltype = AA   length = 9
FEATURE                   Location/Qualifiers
source                    1..9
                          mol_type = protein
                          organism = Homo sapiens
SEQUENCE: 7
LLDSILINL  9
```

```
SEQ ID NO: 8              moltype = AA   length = 10
FEATURE                   Location/Qualifiers
source                    1..10
```

```
                         mol_type = protein
                         organism = Homo sapiens
SEQUENCE: 8
AIDPHLLLSV                                                    10

SEQ ID NO: 9            moltype = AA  length = 9
FEATURE                 Location/Qualifiers
source                  1..9
                         mol_type = protein
                         organism = Homo sapiens
SEQUENCE: 9
YLVPHNLET                                                     9

SEQ ID NO: 10           moltype = AA  length = 10
FEATURE                 Location/Qualifiers
source                  1..10
                         mol_type = protein
                         organism = Homo sapiens
SEQUENCE: 10
YLYASLDPNA                                                   10

SEQ ID NO: 11           moltype = AA  length = 9
FEATURE                 Location/Qualifiers
source                  1..9
                         mol_type = protein
                         organism = Homo sapiens
SEQUENCE: 11
AMFGKLMTI                                                     9

SEQ ID NO: 12           moltype = AA  length = 9
FEATURE                 Location/Qualifiers
source                  1..9
                         mol_type = protein
                         organism = Homo sapiens
SEQUENCE: 12
FLLERIAPV                                                     9

SEQ ID NO: 13           moltype = AA  length = 9
FEATURE                 Location/Qualifiers
source                  1..9
                         mol_type = protein
                         organism = Homo sapiens
SEQUENCE: 13
LNADVPEQL                                                     9

SEQ ID NO: 14           moltype = AA  length = 8
FEATURE                 Location/Qualifiers
source                  1..8
                         mol_type = protein
                         organism = Homo sapiens
SEQUENCE: 14
QLITPLVS                                                      8

SEQ ID NO: 15           moltype = AA  length = 10
FEATURE                 Location/Qualifiers
source                  1..10
                         mol_type = protein
                         organism = Homo sapiens
SEQUENCE: 15
KLWSPDEEVS                                                   10

SEQ ID NO: 16           moltype = AA  length = 9
FEATURE                 Location/Qualifiers
source                  1..9
                         mol_type = protein
                         organism = Homo sapiens
SEQUENCE: 16
VINDECYQV                                                     9

SEQ ID NO: 17           moltype = AA  length = 9
FEATURE                 Location/Qualifiers
source                  1..9
                         mol_type = protein
                         organism = Homo sapiens
SEQUENCE: 17
YMAIFALCA                                                     9

SEQ ID NO: 18           moltype = AA  length = 10
FEATURE                 Location/Qualifiers
```

-continued

```
source                   1..10
                         mol_type = protein
                         organism = Homo sapiens
SEQUENCE: 18
KLYTVCDVAL                                                                    10

SEQ ID NO: 19            moltype = AA  length = 10
FEATURE                  Location/Qualifiers
source                   1..10
                         mol_type = protein
                         organism = Homo sapiens
SEQUENCE: 19
YTVCDVALCV                                                                    10

SEQ ID NO: 20            moltype = AA  length = 9
FEATURE                  Location/Qualifiers
source                   1..9
                         mol_type = protein
                         organism = Homo sapiens
SEQUENCE: 20
AYPPGVKEI                                                                     9

SEQ ID NO: 21            moltype = AA  length = 9
FEATURE                  Location/Qualifiers
source                   1..9
                         mol_type = protein
                         organism = Homo sapiens
SEQUENCE: 21
QYLPLALHL                                                                     9

SEQ ID NO: 22            moltype = AA  length = 9
FEATURE                  Location/Qualifiers
source                   1..9
                         mol_type = protein
                         organism = Homo sapiens
SEQUENCE: 22
IFLFITRQL                                                                     9

SEQ ID NO: 23            moltype = AA  length = 9
FEATURE                  Location/Qualifiers
source                   1..9
                         mol_type = protein
                         organism = Homo sapiens
SEQUENCE: 23
QFNRYFYLL                                                                     9

SEQ ID NO: 24            moltype = AA  length = 9
FEATURE                  Location/Qualifiers
source                   1..9
                         mol_type = protein
                         organism = Homo sapiens
SEQUENCE: 24
RYFYLLENL                                                                     9

SEQ ID NO: 25            moltype = AA  length = 9
FEATURE                  Location/Qualifiers
source                   1..9
                         mol_type = protein
                         organism = Homo sapiens
SEQUENCE: 25
FYLLENLAW                                                                     9

SEQ ID NO: 26            moltype = AA  length = 10
FEATURE                  Location/Qualifiers
source                   1..10
                         mol_type = protein
                         organism = Homo sapiens
SEQUENCE: 26
AWVKSYNICF                                                                    10

SEQ ID NO: 27            moltype = AA  length = 9
FEATURE                  Location/Qualifiers
source                   1..9
                         mol_type = protein
                         organism = Homo sapiens
SEQUENCE: 27
IFIQLFRTL                                                                     9

SEQ ID NO: 28            moltype = AA  length = 9
```

-continued

```
FEATURE              Location/Qualifiers
source               1..9
                     mol_type = protein
                     organism = Homo sapiens
SEQUENCE: 28
VFDLIQELF                                                              9

SEQ ID NO: 29        moltype = AA  length = 9
FEATURE              Location/Qualifiers
source               1..9
                     mol_type = protein
                     organism = Homo sapiens
SEQUENCE: 29
LFAIDPHLL                                                              9

SEQ ID NO: 30        moltype = AA  length = 9
FEATURE              Location/Qualifiers
source               1..9
                     mol_type = protein
                     organism = Homo sapiens
SEQUENCE: 30
LWQCFLGRF                                                              9

SEQ ID NO: 31        moltype = AA  length = 10
FEATURE              Location/Qualifiers
source               1..10
                     mol_type = protein
                     organism = Homo sapiens
SEQUENCE: 31
YYQNSIDDKL                                                            10

SEQ ID NO: 32        moltype = AA  length = 9
FEATURE              Location/Qualifiers
source               1..9
                     mol_type = protein
                     organism = Homo sapiens
SEQUENCE: 32
TYESLLQCL                                                              9

SEQ ID NO: 33        moltype = AA  length = 9
FEATURE              Location/Qualifiers
source               1..9
                     mol_type = protein
                     organism = Homo sapiens
SEQUENCE: 33
IFRNTGHKI                                                              9

SEQ ID NO: 34        moltype = AA  length = 9
FEATURE              Location/Qualifiers
source               1..9
                     mol_type = protein
                     organism = Homo sapiens
SEQUENCE: 34
IFEPLSRSL                                                              9

SEQ ID NO: 35        moltype = AA  length = 16
FEATURE              Location/Qualifiers
source               1..16
                     mol_type = protein
                     organism = Homo sapiens
SEQUENCE: 35
ASEFFLRNPN KDVRLL                                                     16

SEQ ID NO: 36        moltype = AA  length = 19
FEATURE              Location/Qualifiers
source               1..19
                     mol_type = protein
                     organism = Homo sapiens
SEQUENCE: 36
LKDIFLFITR QLKGLEDTK                                                  19

SEQ ID NO: 37        moltype = AA  length = 17
FEATURE              Location/Qualifiers
source               1..17
                     mol_type = protein
                     organism = Homo sapiens
SEQUENCE: 37
FNRYFYLLEN LAWVKSY                                                    17
```

-continued

```
SEQ ID NO: 38              moltype = AA  length = 15
FEATURE                    Location/Qualifiers
source                     1..15
                           mol_type = protein
                           organism = Homo sapiens
SEQUENCE: 38
NLAWVKSYNI CFELE                                                15

SEQ ID NO: 39              moltype = AA  length = 18
FEATURE                    Location/Qualifiers
source                     1..18
                           mol_type = protein
                           organism = Homo sapiens
SEQUENCE: 39
NEIFIQLFRT LFSVINNS                                             18

SEQ ID NO: 40              moltype = AA  length = 17
FEATURE                    Location/Qualifiers
source                     1..17
                           mol_type = protein
                           organism = Homo sapiens
SEQUENCE: 40
TLFSVINNSH NKKVQMH                                              17

SEQ ID NO: 41              moltype = AA  length = 18
FEATURE                    Location/Qualifiers
source                     1..18
                           mol_type = protein
                           organism = Homo sapiens
SEQUENCE: 41
NKKVQMHMLD LMSSIIME                                             18

SEQ ID NO: 42              moltype = AA  length = 19
FEATURE                    Location/Qualifiers
source                     1..19
                           mol_type = protein
                           organism = Homo sapiens
SEQUENCE: 42
LDSILINLIP AHKNLNKQS                                            19

SEQ ID NO: 43              moltype = AA  length = 23
FEATURE                    Location/Qualifiers
source                     1..23
                           mol_type = protein
                           organism = Homo sapiens
SEQUENCE: 43
IQELFAIDPH LLLSVMPQLE FKL                                       23

SEQ ID NO: 44              moltype = AA  length = 18
FEATURE                    Location/Qualifiers
source                     1..18
                           mol_type = protein
                           organism = Homo sapiens
SEQUENCE: 44
GEERLAVVRL LAKLFGSK                                             18

SEQ ID NO: 45              moltype = AA  length = 19
FEATURE                    Location/Qualifiers
source                     1..19
                           mol_type = protein
                           organism = Homo sapiens
SEQUENCE: 45
HDVIVTIITA AKRDLALVN                                            19

SEQ ID NO: 46              moltype = AA  length = 19
FEATURE                    Location/Qualifiers
source                     1..19
                           mol_type = protein
                           organism = Homo sapiens
SEQUENCE: 46
SAMFGKLMTI AKNLPDPGK                                            19

SEQ ID NO: 47              moltype = AA  length = 16
FEATURE                    Location/Qualifiers
source                     1..16
                           mol_type = protein
                           organism = Homo sapiens
SEQUENCE: 47
AQDFVKKFNQ VLGDDE                                               16
```

-continued

```
SEQ ID NO: 48             moltype = AA   length = 21
FEATURE                   Location/Qualifiers
source                    1..21
                          mol_type = protein
                          organism = Homo sapiens
SEQUENCE: 48
ECLEAISALV KLMNKSIEGT A                                           21

SEQ ID NO: 49             moltype = AA   length = 15
FEATURE                   Location/Qualifiers
source                    1..15
                          mol_type = protein
                          organism = Homo sapiens
SEQUENCE: 49
PTSFHSAETY ESLLQ                                                  15

SEQ ID NO: 50             moltype = AA   length = 18
FEATURE                   Location/Qualifiers
source                    1..18
                          mol_type = protein
                          organism = Homo sapiens
SEQUENCE: 50
EAAIQIFRNT GHKIETDL                                               18

SEQ ID NO: 51             moltype = AA   length = 18
FEATURE                   Location/Qualifiers
source                    1..18
                          mol_type = protein
                          organism = Homo sapiens
SEQUENCE: 51
LPQIRSTLIP ILHQKAKR                                               18

SEQ ID NO: 52             moltype = AA   length = 16
FEATURE                   Location/Qualifiers
source                    1..16
                          mol_type = protein
                          organism = Homo sapiens
SEQUENCE: 52
LIPILHQKAK RGTPHQ                                                 16

SEQ ID NO: 53             moltype = AA   length = 20
FEATURE                   Location/Qualifiers
source                    1..20
                          mol_type = protein
                          organism = Homo sapiens
SEQUENCE: 53
KQAVHCIHAI FTNKEVQLAQ                                             20

SEQ ID NO: 54             moltype = AA   length = 15
FEATURE                   Location/Qualifiers
source                    1..15
                          mol_type = protein
                          organism = Homo sapiens
SEQUENCE: 54
ASPMKSVVAN FIVKD                                                  15

SEQ ID NO: 55             moltype = AA   length = 19
FEATURE                   Location/Qualifiers
source                    1..19
                          mol_type = protein
                          organism = Homo sapiens
SEQUENCE: 55
VLAKVQAIKL LVRWLLGMK                                              19

SEQ ID NO: 56             moltype = AA   length = 18
FEATURE                   Location/Qualifiers
source                    1..18
                          mol_type = protein
                          organism = Homo sapiens
SEQUENCE: 56
KLLVRWLLGM KNNQSKSA                                               18

SEQ ID NO: 57             moltype = AA   length = 20
FEATURE                   Location/Qualifiers
source                    1..20
                          mol_type = protein
                          organism = Homo sapiens
SEQUENCE: 57
```

-continued

```
SANSTLRLLS AMLVSEGDLT                                              20

SEQ ID NO: 58          moltype = AA   length = 18
FEATURE                Location/Qualifiers
source                 1..18
                       mol_type = protein
                       organism = Homo sapiens
SEQUENCE: 58
KSDMSRLRLA AGSAIMKL                                                18

SEQ ID NO: 59          moltype = AA   length = 19
FEATURE                Location/Qualifiers
source                 1..19
                       mol_type = protein
                       organism = Homo sapiens
SEQUENCE: 59
CYQVRQIFAQ KLHKALVKL                                               19

SEQ ID NO: 60          moltype = AA   length = 15
FEATURE                Location/Qualifiers
source                 1..15
                       mol_type = protein
                       organism = Homo sapiens
SEQUENCE: 60
PLEYMAIFAL CAKDP                                                   15

SEQ ID NO: 61          moltype = AA   length = 18
FEATURE                Location/Qualifiers
source                 1..18
                       mol_type = protein
                       organism = Homo sapiens
SEQUENCE: 61
AHARQCLLKN ISIRREYI                                                18

SEQ ID NO: 62          moltype = AA   length = 15
FEATURE                Location/Qualifiers
source                 1..15
                       mol_type = protein
                       organism = Homo sapiens
SEQUENCE: 62
RREYIKQNPM ATEKL                                                   15

SEQ ID NO: 63          moltype = AA   length = 22
FEATURE                Location/Qualifiers
source                 1..22
                       mol_type = protein
                       organism = Homo sapiens
SEQUENCE: 63
ECLWFMLEVL MTKNENNSHA FM                                           22

SEQ ID NO: 64          moltype = AA   length = 23
FEATURE                Location/Qualifiers
source                 1..23
                       mol_type = protein
                       organism = Homo sapiens
SEQUENCE: 64
SHAFMKKMAE NIKLTRDAQS PDE                                          23

SEQ ID NO: 65          moltype = AA   length = 23
FEATURE                Location/Qualifiers
source                 1..23
                       mol_type = protein
                       organism = Homo sapiens
SEQUENCE: 65
KSYISEETRV LLLTGKPKPA GVL                                          23

SEQ ID NO: 66          moltype = AA   length = 18
FEATURE                Location/Qualifiers
source                 1..18
                       mol_type = protein
                       organism = Homo sapiens
SEQUENCE: 66
PAGVLGAVNK PLSATGRK                                                18

SEQ ID NO: 67          moltype = AA   length = 17
FEATURE                Location/Qualifiers
source                 1..17
                       mol_type = protein
                       organism = Homo sapiens
```

```
SEQUENCE: 67
ENPVRIISVT PVKNIDP                                                    17

SEQ ID NO: 68          moltype = DNA   length = 21
FEATURE                Location/Qualifiers
misc_feature           1..21
                       note = primer sense
source                 1..21
                       mol_type = other DNA
                       organism = synthetic construct
SEQUENCE: 68
gtaaggtggc tgttgggtat g                                              21

SEQ ID NO: 69          moltype = DNA   length = 24
FEATURE                Location/Qualifiers
misc_feature           1..24
                       note = primer antisense
source                 1..24
                       mol_type = other DNA
                       organism = synthetic construct
SEQUENCE: 69
ggctagcagg tgaatcatgt atgg                                           24

SEQ ID NO: 70          moltype = DNA   length = 18
FEATURE                Location/Qualifiers
misc_feature           1..18
                       note = GAPDH primer
source                 1..18
                       mol_type = other DNA
                       organism = synthetic construct
SEQUENCE: 70
gggctgcttt taactctg                                                  18

SEQ ID NO: 71          moltype = DNA   length = 18
FEATURE                Location/Qualifiers
misc_feature           1..18
                       note = GAPDH primer
source                 1..18
                       mol_type = other DNA
                       organism = synthetic construct
SEQUENCE: 71
ccaggaaatg agcttgac                                                  18

SEQ ID NO: 72          moltype = DNA   length = 29
FEATURE                Location/Qualifiers
misc_feature           1..29
                       note = primer sense
source                 1..29
                       mol_type = other DNA
                       organism = synthetic construct
SEQUENCE: 72
gcggccgcat ggacttcacc gcgcagccc                                      29

SEQ ID NO: 73          moltype = DNA   length = 29
FEATURE                Location/Qualifiers
misc_feature           1..29
                       note = primer antisense
source                 1..29
                       mol_type = other DNA
                       organism = synthetic construct
SEQUENCE: 73
ctcgagttac ctttgtaagt caatttgtc                                      29

SEQ ID NO: 74          moltype = AA   length = 9
FEATURE                Location/Qualifiers
source                 1..9
                       mol_type = protein
                       organism = Homo sapiens
SEQUENCE: 74
SLYNTYATL                                                            9

SEQ ID NO: 75          moltype = AA   length = 9
FEATURE                Location/Qualifiers
source                 1..9
                       mol_type = protein
                       organism = Homo sapiens
SEQUENCE: 75
NLIPAHKNL                                                            9
```

-continued

```
SEQ ID NO: 76          moltype = AA  length = 10
FEATURE                Location/Qualifiers
source                 1..10
                       mol_type = protein
                       organism = Homo sapiens
SEQUENCE: 76
KECLWFMLEV                                                         10

SEQ ID NO: 77          moltype = AA  length = 10
FEATURE                Location/Qualifiers
source                 1..10
                       mol_type = protein
                       organism = Homo sapiens
SEQUENCE: 77
FLGRFNDIHV                                                         10

SEQ ID NO: 78          moltype = AA  length = 10
FEATURE                Location/Qualifiers
source                 1..10
                       mol_type = protein
                       organism = Homo sapiens
SEQUENCE: 78
LLLPLEYMAI                                                         10

SEQ ID NO: 79          moltype = AA  length = 10
FEATURE                Location/Qualifiers
source                 1..10
                       mol_type = protein
                       organism = Homo sapiens
SEQUENCE: 79
SLDPNAVKAL                                                         10

SEQ ID NO: 80          moltype = AA  length = 9
FEATURE                Location/Qualifiers
source                 1..9
                       mol_type = protein
                       organism = Homo sapiens
SEQUENCE: 80
KLKDIFLFI                                                          9

SEQ ID NO: 81          moltype = AA  length = 10
FEATURE                Location/Qualifiers
source                 1..10
                       mol_type = protein
                       organism = Homo sapiens
SEQUENCE: 81
LLSLLPEYVV                                                         10

SEQ ID NO: 82          moltype = AA  length = 9
FEATURE                Location/Qualifiers
source                 1..9
                       mol_type = protein
                       organism = Homo sapiens
SEQUENCE: 82
KMAENIKLT                                                          9

SEQ ID NO: 83          moltype = AA  length = 10
FEATURE                Location/Qualifiers
source                 1..10
                       mol_type = protein
                       organism = Homo sapiens
SEQUENCE: 83
QVLVLGRSSV                                                         10

SEQ ID NO: 84          moltype = AA  length = 9
FEATURE                Location/Qualifiers
source                 1..9
                       mol_type = protein
                       organism = Homo sapiens
SEQUENCE: 84
RYLRDQQLL                                                          9

SEQ ID NO: 85          moltype = AA  length = 18
FEATURE                Location/Qualifiers
source                 1..18
                       mol_type = protein
                       organism = Homo sapiens
SEQUENCE: 85
YVDRFFKTLR AEQATQDV                                                18
```

-continued

```
SEQ ID NO: 86        moltype = AA  length = 4
FEATURE              Location/Qualifiers
source               1..4
                     mol_type = protein
                     organism = synthetic construct
SEQUENCE: 86
NKRK                                                           4
```

The invention claimed is:

1. An immune inducer composition comprising the following (i) and (ii):
   (i) at least one polypeptide consisting of the amino acid sequence represented by one of SEQ ID NOs: 5, 6, 7, 9, 10, 12-15, and 17-34; and
   (ii) an effective amount of an adjuvant.

2. The immune inducer composition according to claim 1, wherein the polypeptide (i) binds to a MHC class I molecule.

3. The immune inducer composition according to claim 2, wherein the polypeptide (i) is SEQ ID NO: 6.

4. An immune inducer composition comprising the following (i) and (ii):
   (i) at least one polypeptide consisting of the amino acid sequence represented by one of SEQ ID NOs: 35-67; and
   (ii) an effective amount of an adjuvant.

5. The immune inducer composition according to claim 1, further comprising an immunopotentiator.

* * * * *